United States Patent
Nagashima et al.

(10) Patent No.: US 10,239,896 B2
(45) Date of Patent: Mar. 26, 2019

(54) HYDROSILYLATION IRON CATALYST

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Fukuoka (JP); Yusuke Sunada, Fukuoka (JP); Daisuke Noda, Fukuoka (JP); Hiroe Soejima, Fukuoka (JP); Koji Sakuta, Annaka (JP)

(73) Assignees: KYUSHU UNIVERSITY, NATIONAL UNIVERSITY CORPORATION, Fukuoka-Shi (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/504,736

(22) PCT Filed: Aug. 19, 2015

(86) PCT No.: PCT/JP2015/073185
§ 371 (c)(1),
(2) Date: Feb. 17, 2017

(87) PCT Pub. No.: WO2016/027819
PCT Pub. Date: Feb. 25, 2016

(65) Prior Publication Data
US 2017/0260216 A1  Sep. 14, 2017

(30) Foreign Application Priority Data

Aug. 19, 2014 (JP) .................... 2014-166596

(51) Int. Cl.
| | |
|---|---|
| *C07F 7/08* | (2006.01) |
| *B01J 31/22* | (2006.01) |
| *C07F 7/18* | (2006.01) |
| *C07B 47/00* | (2006.01) |
| *C07F 15/02* | (2006.01) |
| *B01J 31/18* | (2006.01) |
| *C07B 61/00* | (2006.01) |

(52) U.S. Cl.
CPC .............. *C07F 7/0879* (2013.01); *B01J 31/18* (2013.01); *B01J 31/181* (2013.01); *B01J 31/1815* (2013.01); *B01J 31/22* (2013.01); *B01J 31/2273* (2013.01); *B01J 31/2291* (2013.01); *B01J 31/2295* (2013.01); *C07B 47/00* (2013.01); *C07F 7/0829* (2013.01); *C07F 7/18* (2013.01); *C07F 15/02* (2013.01); *B01J 2231/323* (2013.01); *B01J 2531/0205* (2013.01); *B01J 2531/842* (2013.01); *C07B 61/00* (2013.01)

(58) Field of Classification Search
CPC ......... C07F 7/0879; C07F 15/02; B01J 31/22; C07B 47/00
USPC ........................................................ 556/450
See application file for complete search history.

(56) References Cited

U.S. PATENT DOCUMENTS

| | | | |
|---|---|---|---|
| 4,992,573 A | 2/1991 | Lewis | |
| 5,389,404 A | 2/1995 | Armstrong | |
| 5,523,436 A | 6/1996 | Dauth et al. | |
| 5,561,231 A | 10/1996 | Dauth et al. | |
| 6,124,418 A | 9/2000 | Crivello et al. | |
| 6,303,728 B1 | 10/2001 | Hagimori et al. | |
| 6,492,525 B1 | 12/2002 | Bertrand et al. | |
| 6,737,531 B1 | 5/2004 | Dioumaev et al. | |
| 6,803,440 B2 | 10/2004 | Marko et al. | |
| 7,019,145 B2 | 3/2006 | Buisine et al. | |
| 7,563,741 B2 | 7/2009 | Brummer et al. | |
| 7,803,893 B2 | 9/2010 | Hofmann et al. | |
| 8,124,711 B2 | 2/2012 | Hofmann et al. | |
| 8,236,915 B2 | 8/2012 | Delis et al. | |
| 8,415,443 B2 | 4/2013 | Delis et al. | |
| 8,895,770 B2 | 11/2014 | Lewis et al. | |

(Continued)

FOREIGN PATENT DOCUMENTS

| | | |
|---|---|---|
| CN | 102351907 A | 2/2012 |
| CN | 102516314 A | 6/2012 |

(Continued)

OTHER PUBLICATIONS

Bart et al., J. Amer. Chem. Soc., 2004, 126(42), 13794-13807.*

(Continued)

*Primary Examiner* — Clinton A Brooks
*Assistant Examiner* — Kofi Adzamli
(74) *Attorney, Agent, or Firm* — Birch, Stewart, Kolasch & Birch, LLP

(57) ABSTRACT

A hydrosilylation iron catalyst prepared from a two-electron ligand (L) and a mononuclear, binuclear, or trinuclear complex of iron indicated by formula (1), Fe having bonds with carbon atoms included in X and the total number of Fe-carbon bonds being 2-10. As a result of using iron, the hydrosilylation iron catalyst is advantageous from a cost perspective as well as being easily synthesized. Hydrosilylation reactions can be promoted under mild conditions by using this catalyst.

$$Fe(X)_a \quad (1)$$

(in the formula, each X independently indicates a C2-30 ligand that may include an unsaturated group excluding carbonyl groups (CO groups) and cyclopentadienyl groups, however at least one X includes an unsaturated group, a indicates an integer of 2-4 per Fe atom.)

16 Claims, 6 Drawing Sheets

(56) References Cited

U.S. PATENT DOCUMENTS

| | | |
|---|---|---|
| 9,073,950 B2 | 7/2015 | Kownacka et al. |
| 9,480,977 B2 | 11/2016 | Brandstadt et al. |
| 2004/0236054 A1 | 11/2004 | George et al. |
| 2011/0160454 A1 | 6/2011 | Yoo et al. |
| 2014/0249311 A1 | 9/2014 | Brandstadt et al. |

FOREIGN PATENT DOCUMENTS

| | | |
|---|---|---|
| EP | 2 114 977 A1 | 11/2009 |
| EP | 3 269 724 A1 | 1/2018 |
| FR | 2 911 876 A1 | 8/2008 |
| JP | 1-315344 A | 12/1989 |
| JP | 6-136126 A | 5/1994 |
| JP | 6-263780 A | 9/1994 |
| JP | 7-149780 A | 6/1995 |
| JP | 2001-131231 A | 5/2001 |
| JP | 3174616 B2 | 6/2001 |
| JP | 3599669 B2 | 12/2004 |
| JP | 3854151 B2 | 12/2006 |
| JP | 4007467 B2 | 11/2007 |
| JP | 4249702 B2 | 4/2009 |
| JP | 4934190 B2 | 5/2012 |
| JP | 5032561 B2 | 9/2012 |
| JP | 2012-532884 A | 12/2012 |
| JP | 2012-532885 A | 12/2012 |
| JP | 2013-544824 A | 12/2013 |
| JP | 2014-502271 A | 1/2014 |
| JP | 2014-503507 A | 2/2014 |
| WO | WO 2008/095785 A1 | 8/2008 |
| WO | WO 2010/016416 A1 | 2/2010 |
| WO | WO 2013/043783 A2 | 3/2013 |
| WO | WO 2013/043785 A2 | 3/2013 |
| WO | WO 2013/043787 A2 | 3/2013 |
| WO | WO 2013/043846 A1 | 3/2013 |
| WO | WO 2013/043912 A2 | 3/2013 |
| WO | WO 2013/081794 A1 | 6/2013 |
| WO | WO 2014/021908 A1 | 2/2014 |

OTHER PUBLICATIONS

Hashimoto et al., Organometallics 2012, 31, 4474-4479. (Year: 2012).*

Adams et al., "The Catalytic Activity of Transition Metal Complexes of Sterically Hindered Isocyanides", Journal of Molecular Catalysis, 1985, vol. 29, pp. 201-208.

Bart et al., "Preparation and Molecular and Electronic Structures of Iron(0) Dinitrogen and Silane Complexes and Their Application to Catalytic Hydrogenation and Hydrosilation", Journal of the American Chemical Society, 2004, vol. 126, No. 42, pp. 13794-13807, column of Abstract, column of Synthesis and Characterization of Potential Catalytic Intermediates, column of General Hydrosilation Procedure.

Brookhart et al., "Mechanism of a Cobalt(III)-Catalyzed Olefin Hydrosilation Reaction: Direct Evidence for a Silyl Migration Pathway", J. Am. Chem. Soc., 1993, vol. 115, pp. 2151-2156.

Buitrago et al., "Selective hydrosilylation of ketones catalyzed by in situ-generated iron NHC complexes", Applied Organometallic Chemistry, 2011, vol. 25, No. 10, pp. 748-752

Chalk et al., "Dicobalt Octacarbonyl as a Catalyst for Hydrosilation of Olefins", J .Am. Chem. Soc., 1965, vol. 87, No. 16, pp. 1133.

Chalk et al., "Homogeneous Catalysis. IV. Some Reactions of Silicon Hydrides in the Presence of Cobalt Carbonyls", Journal of the American Chemical Society, Mar. 29, 1967, vol. 89, No. 7, pp. 1640-1647.

Chalk, "The Hydrosilation of Olefins Catalyzed by Some Rhodium and Cobalt Complexes", Journal of Organometallic Chemistry, 1970, vol. 21, pp. 207-213.

Chatani et al., "The $CO_2(C0)_8$-Catalyzed Hydrosilylation of Oxygen-Containing Olefins: Silylmetalation as a Key Step", Chemistry Letters, 2000, pp. 14-15.

Cornish et al., "Homogeneous Catalysis VI .Hydrosilylation Using Tris(Pentanedionato)Rhodium(III) or Tetrakis(μ-Acetato)Dirhodium(III) as Catalyst", Journal of Organometallic Chemistry, 1979, vol. 172, pp. 153-163.

Hashimoto et al., "Synthesis of Bis(N-heterocyciic carbene) Complexes of Iron(II) and Their Application in Hydrosilylation and Transfer Hydrogenation", Organometallics, 2012, vol. 31, No. 12, pp. 4474-4479.

Hill et al., "Rhodium Carbene Complexes as Hydrosilylation Catalysts", Journal of Organometallic Chemistry, 1977, vol. 137, pp. 293-300.

Hyder et al., "Oligomerization and regioselective hydrosilylation of styrenes catalyzed by cationic allyl nickel complexes bearing allylphosphine ligands", Dalton Trans., 2007, pp. 3000-3009.

Imlinger et al., "Rh(1,3-bis(2,4,6-trimethylphenyl)-3,4,5,6-tetrahydropyrimidin-2-ylidene)(COD) tetrafluoroborate, an unsymmetrical Rh-homoazallylcarbene: synthesis. X-ray structure and reactivity in carbonyl arylation and hydrosilylation reactions", Journal of Organometallic Chemistry, 2005, vol. 690, pp. 4433-4440.

International Search Report, issued in PCT/JP2015/073185, dated Nov. 10, 2015.

Junquera et al., "R-Allyl Nickel(II) Complexes with Chelating N-Heterocyclic Carbenes: Synthesis, Structural Characterization, and Catalytic Activity", Organometallics, 2012, vol. 31, pp. 2175-2183.

Kakiuchi et al., "Completely selective synthesis of ( E)-β-( triethylsilyl)styrenes by $Fe_2(CO)_2$-catalyzed reaction of styrenes with triethylsilane", Journal of Organometallic Chemistry, 1993, vol. 456, pp. 45-47.

Kamata et al., "Catalytic Hydrosilylation of Alkenes by Iron Complexes Containing Terpyridine Derivatives as Ancillary Ligands", Organometallics. 2012, vol. 31, pp. 3825-3828.

Kiso et al., "Silicon Hydrides and Nickel Complexes I. Phosphine-Nickel(II) Complexes as Hydrosilylation Catalysts", Journal of Organometallic Chemistry, 1973, vol. 50, pp. 297-310.

Li et al., "Synthesis of rhodium N-heterocyciic carbene complexes and their catalytic activity in the hydrosilylation of alkenes in ionic liquid medium", Journal of Organometallic Chemistry, 2011, vol. 696, pp. 2116-2121.

Lipschutz et al., "Synthesis and reactivity of a conveniently prepared two-coordinate bis(amido) nickel(II) complex", Chem. Commun., 2012, vol. 48, pp. 7146-7148.

Maciejewski et al., "Catalysis of hydrosilylation Part XXXIV. High catalytic efficiency of the nickel equivalent of Karstedt catalyst [{Ni(η-$CH_2$=$CHSiMe_2$)$_2$O}$_2$ {μ-(η-$CH_2$=$CHSiMe_2$)$_2$O}]", Journal of Organometallic Chemistry, 2000, vol. 597, pp. 175-181.

Magomedov et al., "Hydrosilylation of Olefins in the Presence of Metal Carbonyls", Journal of Organometallic Chemistry, 1978, vol. 149, pp. 29-36.

Mo et al., "Anchoring of Silyl Donors on a N-Heterocyclic Carbene through the Cobalt-Mediated Silylation of Benzylic C—H Bonds", Angewandte Chemie. International Edition, 2013, vol. 52, pp. 10845-10849.

Naumov et al., "Selective Dehydrogenative Silylation—Hydrogenation Reaction of Divinyldisiloxane with Hydrosilane Catalyzed by an Iron Complex", Journal of the American Society, 2012, vol. 134, pp. 804-807.

Nesmeyanov et al., "Addition, Substitution, and Telomerization Reactions of Olefins in the Presence of Metal Carbonyls or Colloidal Iron", Tetrahedron, 1962, vol. 17, pp. 61-68.

Reichel et al., "Photochemistry of Cobalt Carbonyl Complexes Having a Cobalt-Silicon Bond and Its Importance in Activation of Catalysis", Inorg. Chem., 1980, vol. 19, pp. 3858-3860.

Schroeder et al., "Pentacarbonyliron(0) Photocatalyzed Reactions of Trialkylsilanes With Alkenes", Journal of Organometallic Chemistry, 1977, vol. 128, pp. 345-358.

Takeshita et al., "The Catalyzed Reaction of α,β-Unsaturated Esters with Various Hydrosilanes", J . Org. Chem., 1987, vol. 52, pp. 4864-4868.

Tondreau et al., "Enantiopure Pyridine Bis(oxazoline) "Pybox" and Bis(oxazoline) "Box" Iron Dialkyl Complexes: Comparison to Bis(imino)pyridine Compounds and Application to Catalytic

(56) References Cited

OTHER PUBLICATIONS

Hydrosilylation of Ketones", Organometallics, 2009, vol. 28, No. 13, pp. 3928-39404 column of Catalytic Hydrosilylation with Pybox- and Box-Ligated Iron Dialkyl Compounds, Scheme 4, Table 4.

Tondreau et al., "Iron Catalysts for Selective Anti-Markovnikov Alkene Hydrosilylation Using Tertiary Silanes", Science, 2012, vol. 335, pp. 567-570.

Tondreau et al., "Synthesis, Electronic Structure, and Alkene Hydrosilylation Activity of Terpyridine and Bis(imino)pyridine Iron Dialkyl Complexes", Organometallics, 2012, vol. 31, pp. 4886-4893.

Truscott et al., "Well-defined NHC-rhodium hydroxide complexes as alkene hydrosilyiation and dehydrogenative silylation catalysts", Dalton Transactions, 2013, vol. 42, pp. 270-276.

Written Opinion of the International Searching Authority (PCT/ISA/237), issued in PCT/JP2015/073185, dated Nov. 10, 2015.

European Search Report for Appl. No. 15833178.5 dated Feb. 8, 2018.

Noda, D., et al, "Effect of TMEDA on Iron-Catalyzed Coupling Reactions of ArMgX with Alkyl Halides," J. Am. Chem. Soc., May 6, 2009, vol. 131, No. 17, pp. 6078-6079.

Sunada, Y., et al, "Catalyst design for iron-promoted reductions: an iron disilyl-dicarbonyl complex bearing weakly coordinating n2-(H-Si) moieties," Dalton Trans., Jan. 1, 2013, vol. 42, No. 48, pp. 16687-16692.

Sunada, Y., et al, "Combinatorial Approach to the Catalytic Hydrosilylation of Styrene Derivatives: Catalyst Systems Composed of Organoiron(0) or (II) Precursors and Isocyanides," Organometallics, Jun. 22, 2015, vol. 34, No. 12, pp. 2896-2906.

\* cited by examiner

HYDROSILYLATION IRON CATALYST

TECHNICAL FIELD

This invention relates to a hydrosilylation iron catalyst and more particularly, to a hydrosilylation iron catalyst formed from an iron complex compound serving as a catalyst precursor and a two-electron ligand.

BACKGROUND ART

Hydrosilylation reaction which is addition reaction of a Si—H functional compound to a compound having a carbon-carbon double bond or triple bond is a useful means for the synthesis of organosilicon compounds and an industrially important synthesis reaction.

As the catalyst for hydrosilylation reaction, Pt, Pd and Rh compounds are known. Among others, Pt compounds as typified by Speier catalyst and Karstedt catalyst are most commonly used.

While several problems arise with reaction in the presence of Pt compounds as the catalyst, one problem is that upon addition of a Si—H functional compound to terminal olefin, a side reaction due to internal rearrangement of olefin takes place. Since this system does not exert addition reactivity to the internal olefin, unreacted olefin is left in the addition product. To drive the reaction to completion, it is necessary to use an excess amount of olefin in advance by taking into account the fraction left as a result of side reaction.

Another problem is that the selectivity of α- and β-adducts is low depending on the type of olefin.

The most serious problem is that all the center metals Pt, Pd and Rh are quite expensive noble metal elements. As metal compound catalysts which can be used at lower cost are desired, a number of research works have been made thereon.

With regard to hydrosilylation reaction in the presence of iron complex catalysts, for example, reaction in the presence of iron-carbonyl complexes $(Fe(CO)_5, Fe_3(CO)_{12})$ is known from Non-Patent Document 1, although this reaction requires reaction conditions including as high a temperature as 160° C. or light irradiation (Non-Patent Document 2).

For these iron-carbonyl complexes, it is reported in Non-Patent Document 3 and Patent Document 1 that dehydrogenation silylated products are obtained rather than the addition reaction.

Also Non-Patent Document 4 and Patent Document 2 report a reaction of methylvinyldisiloxane and methylhydrogendisiloxane in the presence of an iron-carbonyl complex coordinated with a cyclopentadienyl group. Since dehydrogenation silylation reaction takes place along with the relevant reaction, the selectivity of addition reaction is low.

With respect to reaction in the presence of an iron catalyst having a terpyridine ligand (Non-Patent Document 5), a large excess of a reducing agent $(NaBHEt_3)$ is necessary as a reaction co-agent. Although $PhSiH_3$, and $Ph_2SiH_2$ add to olefins, more useful trialkylsilanes, alkoxysilanes and siloxanes have poor addition reactivity to olefins.

Non-Patent Document 6 reports that from reaction in the presence of an iron catalyst having a terpyridine ligand and a bistrimethylsilylmethyl group, an addition reaction product is obtained in high yields. This method needs some steps until the catalyst is synthesized, including first synthesizing a terpyridine-iron complex as a catalyst precursor and introducing a bistrimethylsilylmethyl group therein at a low temperature, which steps are not easy industrially.

Also, Non-Patent Documents 7 and 8 report iron complexes having a bisiminopyridine ligand. It is disclosed that they exhibit high reactivity to alkoxysilanes and siloxanes under mild conditions.

The reaction using the complex, however, suffers from several problems including low reactivity with internal olefin, the use of sodium amalgam consisting of water-prohibitive sodium and highly toxic mercury and requiring careful handling (or use of water-prohibitive $NaBEt_3H$) for complex synthesis, low stability of the complex compound itself, a need for a special equipment like a glove box for handling, and a need for storage in an inert gas atmosphere such as nitrogen at low temperature.

Non-Patent Documents 9 to 14 report examples of reaction in the presence of cobalt-carbonyl complexes (e.g., $Co_2(CO)_8$), but they are unsatisfactory in reaction yield and reaction molar ratio. No reference is made to addition reactivity to siloxanes.

Also an example of reaction of olefin with trialkylsilane in the presence of a cobalt-carbonyl complex substituted with a trialkylsilyl group is reported in Non-Patent Document 15, but the yield is low and the selectivity is low.

Non-Patent Document 16 reports reaction of olefin with trialkylsilane in the presence of a cobalt-phosphite complex coordinated with a cyclopentadienyl group, and Non-Patent Document 17 reports reaction of olefin with trihydrophenylsilane in the presence of a cobalt complex coordinated with N-heterocyclocarbene. Because of low stability, these complex compounds require a special equipment like a glove box for handling and an inert gas atmosphere and a low temperature for storage.

Also Patent Documents 3 to 6 report iron, cobalt and nickel catalysts having terpyridine, bisiminopyridine and bisiminoquinoline ligands. Like the above-cited Non-Patent Documents 6 to 8, there are problems including industrial difficulty of synthesis of a catalyst precursor or synthesis of the complex catalyst from the precursor, low stability of the complex compound itself, and a need for a special equipment for handling.

Patent Document 7 discloses a method of conducting reaction in the presence of a complex catalyst having a bisiminoquinoline ligand, using Mg(butadiene).2THF or $NaEt_3BH$ as the catalyst activator. There are the same problems as above and the yield of the desired product is less than satisfactory.

Many examples of the nickel complex catalyst are reported. For example, a catalyst having a phosphine ligand (Non-Patent Document 18) lacks in selectivity and requires careful handling and storage.

With a vinylsiloxane-coordinated catalyst (Non-Patent Document 19), a dehydrogenation silylated product becomes predominant, indicating low selectivity of addition reaction.

With an allylphosphine-coordinated catalyst (Non-Patent Document 20), the yield is low, and trihydrophenylsilane is not a substrate of industrial worth.

A bisamide-bearing catalyst (Non-Patent Document 21) needs careful handling and storage, and dihydrodiphenylsilane is not a substrate of industrial worth.

A catalyst having N-heterocyclocarbene ligand (Non-Patent Document 22) has low selectivity of reaction, and trihydrophenylsilane is not of industrial worth.

Many rhodium complex catalysts are reported. For example, catalysts having a carbonyl or cyclooctadienyl (COD) group and a N-heterocarbene ligand (Non-Patent Documents 23, 24) are low in stability of complex compound.

Non-Patent Document 25 discloses to conduct reaction in the presence of an ionic liquid in order to enhance reactivity. The step of separating the ionic liquid from the reaction product is necessary. Since the catalyst used therein has a COD group and a N-heterocarbene group as the ligand, the same problems as described above are left.

Also Non-Patent Document 26 reports an exemplary catalyst which allows for preferential progress of dehydrogenation silylation reaction.

Furthermore, Non-Patent Document 27 reports an example in which a carbene compound is added to a complex catalyst to form a catalyst, which is used in hydrosilylation reaction without isolation. A study on reactivity with three types of silanes shows that the order of reactivity is from dimethylphenylsilane, which gives the highest yield (yield 81%), next triethylsilane (yield 66%), to triethoxysilane (yield 40%). The reactivity with triethoxysilane which is of the most industrial worth among the three types of silanes is not so high, while the reactivity with siloxanes is reported nowhere.

In addition, the precursor catalyst having a COD group as the ligand requires careful handling and storage.

On the other hand, Non-Patent Document 28 reports that a rhodium catalyst having an acetylacetonato or acetate group enables addition reaction of triethoxysilane in high yields.

Although this method has the advantage of easy storage and handling of the catalyst, no study is made on reactivity with siloxanes which are more useful from the industrial standpoint.

In addition, rhodium is likewise an expensive noble metal element. Its catalytic function must be further increased to a higher activity before it can be used in practice as a platinum replacement.

The catalysts with their application to organopolysiloxanes being borne in mind include a catalyst having a phosphine ligand (Patent Document 8), a catalyst having an aryl-alkyl-triazenide group (Patent Document 9), a colloidal catalyst (Patent Document 10), a catalyst coordinated with a sulfide group (Patent Document 11), and a catalyst coordinated with an amino, phosphino or sulfide group and an organosiloxane group (Patent Document 12).

However, reactivity is empirically demonstrated with respect to only platinum, palladium, rhodium and iridium which are expensive metal elements. Thus the method is not regarded cost effective.

In Examples of Patent Documents 13 and 14, only well-known platinum catalysts are demonstrated to exert a catalytic effect while the structure which is combined with another metal to exert catalytic activity is indicated nowhere.

Patent Documents 15 to 17 disclose catalysts coordinated with carbene. Patent Document 15 does not discuss whether or not the catalyst is effective to hydrosilylation reaction.

Patent Documents 16 and 17 disclose catalysts coordinated with carbene and vinylsiloxane, but describe only platinum catalysts in Examples.

In addition, the metal catalysts coordinated with carbene require careful handling because the complex compounds have low storage stability.

Likewise, as an example of the catalyst coordinated with carbene, Patent Documents 27 and 28 disclose only platinum catalysts.

Also Patent Document 29 discloses a metal-carbene complex catalyst obtained from reaction of a Ni-carbene complex with a metal precursor. However, the Ni-carbene complex must be separately synthesized. The metal precursor to be reacted is a metal compound having a ligand such as phosphine or COD. The metal precursor having such a ligand is low in storage stability.

Patent Documents 30 and 31 disclose complex catalysts obtained by reacting Pd, Pt and Ni complexes having olefinic ligands with carbene. However, the metal complexes having olefinic ligands except well-known Pt catalysts having vinylsiloxane ligands are low in storage stability.

Patent Document 32 discloses a Co-carbene complex, which is active to hydrosilylation reaction on ketones.

Patent Documents 33 and 34 disclose the application of a metal-carbene complex to curing reaction of organopolysiloxane. Only Pt is referred to as the metal. The synthesis method is reaction of a well-known Pt complex having vinylsiloxane ligand with carbene.

Patent Documents 18 and 19 disclose ruthenium catalysts coordinated with $\eta^6$-arene or $\eta^6$-triene. These catalysts have inferior reactivity to platinum catalysts and require careful handling because the complex compounds have low storage stability.

Patent Documents 20 to 26 disclose a method of mixing a metal salt with a compound which coordinates to the metal and using the product as a catalyst rather than the use of metal complexes as the catalyst. Although these Patent Documents describe the progress of hydrosilylation with several exemplary combinations, the yield and other data are described nowhere, and the extent to which the reaction takes place is not evident.

For example, Patent Documents 21 and 22 describe Examples in which compounds corresponding to carbene are added to halides or trimethylsilylamide salts of Co or Fe. These catalysts are regarded as having reactivity to only phenyltrihydrosilane, but not having reactivity to heptamethyltrisiloxane.

Likewise, Patent Document 25 discloses exemplary Ni compounds and carbene compounds. Only one example is regarded as having activity to addition reaction of heptamethyltrisiloxane, whereas some other examples have activity to only phenyltrihydrosilane, and many other examples have activity to neither phenyltrihydrosilane nor heptamethyltrisiloxane.

Patent Documents 23 and 26 disclose exemplary Ir or Ru compounds and carbene compounds. Of these, only metal compounds having a COD or $\eta^6$-aryl group as an olefinic ligand exhibit reactivity.

In all examples described in Patent Documents 21 to 26, ionic salts or hydride reducing agents are used as the activator. Nevertheless, almost all examples exhibit no catalytic activity.

PRIOR ART DOCUMENTS

Patent Documents

Patent Document 1: WO 2013/081794
Patent Document 2: WO 2010/016416
Patent Document 3: JP-A 2012-532885
Patent Document 4: JP-A 2012-532884
Patent Document 5: JP-A 2013-544824
Patent Document 6: JP-A 2014-502271
Patent Document 7: JP-A 2014-503507
Patent Document 8: JP-A H06-136126
Patent Document 9: JP-A H06-263780
Patent Document 10: JP-A H01-315344
Patent Document 11: JP 3174616
Patent Document 12: JP-A H07-149780
Patent Document 13: JP-A 2001-131231

Patent Document 14: JP 4007467
Patent Document 15: JP 3599669
Patent Document 16: JP 3854151
Patent Document 17: JP 4249702
Patent Document 18: JP 4934190
Patent Document 19: JP 5032561
Patent Document 20: WO 2013/043846
Patent Document 21: WO 2013/043783
Patent Document 22: WO 2013/043912
Patent Document 23: WO 2014/021908
Patent Document 24: WO 2013/081794
Patent Document 25: WO 2013/043785
Patent Document 26: WO 2013/043787
Patent Document 27: CN 102516314
Patent Document 28: US 20110160454
Patent Document 29: CN 102351907
Patent Document 30: WO 2008/095785
Patent Document 31: France 2911876
Patent Document 32: U.S. Pat. No. 6,737,531
Patent Document 33: US 20040236054
Patent Document 34: U.S. Pat. No. 7,019,145

Non-Patent Documents

Non-Patent Document 1: A. N. Nesmeyanov et al., Tetrahedron, 1962, 17, 61
Non-Patent Document 2: M. S. Wrighton et al., J. Organomet. Chem., 1977, 128, 345
Non-Patent Document 3: F. Kakiuchi et al., J. Organomet. Chem., 1993, 456, 45
Non-Patent Document 4: H. Nakazawa et al., J. Am. Chem. Soc., 2012, 134, 804
Non-Patent Document 5: H. Nakazawa et al., Organometallics, 2012, 31, 3825
Non-Patent Document 6: P. J. Chirik et al., Organometallics, 2012, 31, 4886
Non-Patent Document 7: P. J. Chirik et al., J. Am. Chem. Soc., 2004, 126, 13794
Non-Patent Document 8: P. J. Chirik et al., Science, 2012, 335, 567
Non-Patent Document 9: A. J. Chalk et al., J. Am. Chem. Soc., 1965, 87, 1133
Non-Patent Document 10: A. J. Chalk et al., J. Am. Chem. Soc., 1967, 89, 1640
Non-Patent Document 11: A. J. Chalk et al., J. Organomet. Chem., 1970, 21, 207
Non-Patent Document 12: B. A. Izmailov et al., J. Organomet. Chem., 1978, 149, 29
Non-Patent Document 13: N. Sonoda et al., J. Org. Chem., 1987, 52, 4864
Non-Patent Document 14: S. Murai et al., Chem. Lett., 2000, 14
Non-Patent Document 15: M. S. Wrighton et al., Inorg. Chem., 1980, 19, 3858
Non-Patent Document 16: B. E. Grant et al., J. Am. Chem. Soc., 1993, 115, 2151
Non-Patent Document 17: L. Deng et al., Angew. Chem. Int. Ed., 2013, 52, 10845
Non-Patent Document 18: M. Umeno et al., J. Organomet. Chem., 1973, 50, 297
Non-Patent Document 19: I. Kownacki et al., J. Organomet. Chem., 2000, 597, 175
Non-Patent Document 20: P. Valerga et al., Dalton Trans., 2007, 3000
Non-Patent Document 21: T. D. Tilley et al., Chem. Commun., 2012, 48, 7146
Non-Patent Document 22: P. Valerga et al., Organometallics, 2012, 31, 2175
Non-Patent Document 23: T. A. Nile et al., J. Organomet. Chem., 1977, 137, 293
Non-Patent Document 24: M. R. Buchmeiser et al., J. Organomet. Chem., 2005, 690, 4433
Non-Patent Document 25: X. Li et al., J. Organomet. Chem., 2011, 696, 2116
Non-Patent Document 26: S. P. Nolan et al., Dalton Trans., 2013, 42, 270
Non-Patent Document 27: J. M. Walters et al., J. Molecular Catalysis, 1985, 29, 201
Non-Patent Document 28: M. F. Lappert et al., J. Organomet. Chem., 1979, 172, 153

SUMMARY OF THE INVENTION

Problems to be Solved by the Invention

An object of the invention, which has been made under the above-mentioned circumstances, is to provide a hydrosilylation iron catalyst which uses iron, i.e., the most inexpensive element among transition metals, is easy to synthesize, and helps hydrosilylation reaction take place under mild conditions; and a method for preparing an addition compound by hydrosilylation reaction using the same.

Means for Solving the Problems

Making extensive investigations to attain the above objects, the inventors have found that a catalyst which is obtained using a specific iron complex as the catalyst precursor and a two-electron ligand exerts a high activity to hydrosilylation reaction and helps addition reaction take place under mild conditions. The invention is predicated on this finding.

The invention provides a catalyst and a method defined below.

1. A hydrosilylation iron catalyst which is prepared from a two-electron ligand (L) and a mono-, bi- or tri-nuclear complex of iron having the formula (1):

$$Fe(X)_a \qquad (1)$$

wherein X is each independently a $C_2$-$C_{30}$ ligand which may contain an unsaturated group, exclusive of carbonyl (CO) and cyclopentadienyl groups, at least one X contains an unsaturated group, and a is an integer of 2 to 4 per Fe atom, Fe having bonds with carbon atoms in X, and the total number of Fe-carbon bonds being 2 to 10.

2. The hydrosilylation iron catalyst of 1 wherein Fe bonds solely with carbon atoms in X.

3. The hydrosilylation iron catalyst of 1 or 2 wherein each X is a $C_2$-$C_{30}$ ligand containing an unsaturated group.

4. The hydrosilylation iron catalyst of any one of 1 to 3 wherein X is an aryl group, and the total number of Fe-carbon bonds is 2.

5. The hydrosilylation iron catalyst of any one of 1 to 3 which is a mononuclear complex wherein the total number of Fe-carbon bonds is 6 to 10.

6. The hydrosilylation iron catalyst of 5 wherein the total number of Fe-carbon bonds is 10.

7. The hydrosilylation iron catalyst of 5 or 6 wherein X is at least one ligand selected from a cyclic olefin, acyclic olefin, cyclic olefinyl and acyclic olefinyl group having 1 to 5 unsaturated groups in the molecule.

8. The hydrosilylation iron catalyst of any one of 1 to 7 wherein L is at least one two-electron ligand selected from the group consisting of carbonyl, molecular hydrogen, amine, imine, nitrogen-containing heterocycle, phosphine, arsine, alcohol, thiol, ether, sulfide, nitrile, isocyanide, aldehyde, ketone, and carbene.

9. The hydrosilylation iron catalyst of 8 wherein L is at least one two-electron ligand selected from the group consisting of molecular hydrogen, amine, imine, nitrogen-containing heterocycle, phosphine, arsine, alcohol, thiol, ether, sulfide, nitrile, isocyanide, aldehyde, ketone, and carbene.

10. The hydrosilylation iron catalyst of 9 wherein L is at least one two-electron ligand selected from the group consisting of nitrogen-containing heterocycle, isocyanide, and carbene.

11. The hydrosilylation iron catalyst of 10 wherein L is at least one two-electron ligand selected from
an isocyanide compound having the formula (2):

wherein Y is an optionally substituted $C_1$-$C_{30}$ monovalent organic group which may be separated by at least one atom selected from oxygen, nitrogen, sulfur and phosphorus, and
a carbene compound having one or two adjoining nitrogen atoms, represented by the formula (3):

[Chemical Formula 1]

wherein Z is a carbon, nitrogen or oxygen atom, b is 3 when Z is a carbon atom, b is 2 when Z is a nitrogen atom, b is 1 when Z is an oxygen atom, $R^1$ and $R^2$ are each independently a $C_1$-$C_{30}$ alkyl, aryl or aralkyl group which may be substituted with a halogen atom or alkoxy group, any one of $R^1$ and any one of $R^2$ may bond together to form a divalent organic group so that the compound has a cyclic structure, and the compound having a cyclic structure may contain a nitrogen atom and/or unsaturated bond.

12. The hydrosilylation iron catalyst of 11 wherein the carbene compound of formula (3) has the formula (4):

[Chemical Formula 2]

wherein A is a $C_2$-$C_5$ divalent organic group which may contain a nitrogen atom and/or unsaturated bond, $R^1$ and $R^2$ are each independently a $C_1$-$C_{30}$ alkyl, aryl or aralkyl group which may be substituted with a halogen atom or alkoxy group.

13. The hydrosilylation iron catalyst of 10 wherein L is a bisiminopyridine compound or terpyridine compound.

14. The hydrosilylation iron catalyst of any one of 1 to 13 which is prepared in a system where hydrosilylation reaction of a compound having an aliphatic unsaturated bond with a hydrosilane compound having a Si—H group or organohydropolysiloxane compound is carried out.

15. A method for preparing an addition compound comprising the step of carrying out hydrosilylation reaction of a compound having an aliphatic unsaturated bond with a hydrosilane compound having a Si—H bond or organohydropolysiloxane compound in the presence of the hydrosilylation iron catalyst of any one of 1 to 14.

16. The method for preparing an addition compound of 15 wherein the compound having an aliphatic unsaturated bond is an organopolysiloxane having an alkenyl group.

Advantageous Effects of the Invention

The iron complex compound from which the hydrosilylation iron catalyst of the invention is prepared is readily available since it may be synthesized by a well-known method.

The iron complex compound has no catalytic activity for hydrosilylation when used alone, but exhibits catalytic activity when combined with a two-electron ligand.

In order to use an inert iron complex to generate a reactive species, a reducing agent is often necessary. According to the invention, the desired addition reaction by hydrosilylation takes place without a need to separately add a reducing agent because the reactant, hydrosilane itself is utilized as the reducing agent.

The catalyst prepared from the iron complex as precursor and the two-electron ligand may be used after isolation from a catalyst preparation or it may be prepared in situ in a hydrosilylation reaction system and used without isolation.

If hydrosilylation reaction between a compound containing an aliphatic unsaturated group and a silane having a Si—H group or polysiloxane is carried out in the presence of the catalyst prepared from the iron complex as precursor and the two-electron ligand, addition reaction is possible under such conditions as room temperature to 100° C. In particular, addition reaction with industrially useful polysiloxanes, trialkoxysilanes and dialkoxysilanes takes place effectively.

Although the cited documents describe that in the relevant reaction using an iron complex, addition reaction to an unsaturated group and reaction to produce an unsaturated group-containing compound by dehydrogenation silylation reaction often take place at the same time, and dehydrogenation silylation reaction takes place preferentially, the use of the inventive catalyst ensures selective progress of addition reaction to an unsaturated group. The invention is thus quite useful in the silicone industry.

BRIEF DESCRIPTION OF THE DIAGRAMS

EMBODIMENT FOR CARRYING OUT THE INVENTION

Figure 1:
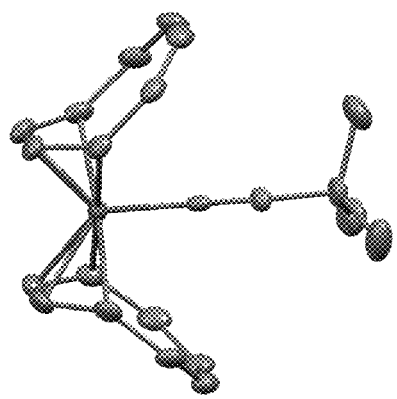
FIG. 1 is a model showing the results of x-ray crystallographic analysis on iron complex A obtained in Synthesis Example 5.

Below the invention is described in more detail.

The invention provides a hydrosilylation iron catalyst which is prepared from a two-electron ligand (L) and a mono-, bi- or tri-nuclear complex of iron having the formula (1):

$$Fe(X)_a \qquad (1)$$

wherein Fe has bonds with carbon atoms in X, and the total number of Fe-carbon bonds is 2 to 10.

In formula (1), X is each independently a $C_2$-$C_{30}$ ligand which may contain an unsaturated group, exclusive of carbonyl (CO) and cyclopentadienyl groups. At least one of ligands X in the iron complex of formula (1) contains an unsaturated group.

The subscript "a" is an integer of 2 to 4 per Fe atom, preferably 2.

The ligand X is a $C_2$-$C_{30}$ ligand which may contain an unsaturated group, exclusive of carbonyl and cyclopentadienyl groups, and is not particularly limited otherwise. Preferably X is selected from among alkyl groups, aryl groups, aralkyl groups, cyclic or acyclic olefin groups, cyclic or acyclic olefinyl groups, which may be substituted with a halogen atom or alkoxy group.

The alkyl groups may be straight, branched or cyclic, preferably $C_1$-$C_{20}$, more preferably $C_1$-$C_{10}$ alkyl groups. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, cyclononyl, norbornyl, and adamantyl.

The aryl groups are preferably $C_6$-$C_{30}$, more preferably $C_6$-$C_{20}$ aryl groups. Examples include phenyl, 1-naphthyl, 2-naphthyl, anthryl, phenanthryl, o-biphenylyl, m-biphenylyl, and p-biphenylyl.

The aralkyl groups are preferably $C_7$-$C_{30}$, more preferably $C_7$-$C_{20}$ aralkyl groups. Examples include benzyl, phenylethyl, phenylpropyl, naphthylmethyl, naphthylethyl, and naphthylpropyl.

Exemplary cyclic olefins include cyclic monoolefins such as cyclobutane, cyclopentene, methylcyclopentene, dimethylcyclopentene, cyclohexene, methylcyclohexene, dimethylcyclohexene, trimethylcyclohexene, tetramethylcyclohexene, cyclooctene, methylcyclooctene, dimethylcyclooctene, tetramethylcyclooctene, cyclodecene, cyclododecene and norbornene; and cyclic polyenes having at least two unsaturated groups in the molecule such as cyclobutadiene, cyclohexadiene, cyclooctadiene, cyclooctatriene, cyclooctatetraene, cyclodecadiene, cyclodecatriene, cyclodecatetraene, and norbornadiene.

Exemplary acyclic olefins include acyclic (chainlike) monoolefins such as ethylene, propylene, butene, isobutene, pentene, hexene, octene, decene and undecene; and acyclic (chainlike) polyenes having at least two unsaturated groups in the molecule such as butadiene, 2-methylbutadiene, pentadiene, methylpentadiene, dimethylpentadiene, hexadiene, hexatriene, octadiene, octatriene, octatetraene, decadiene, decatriene, decatetraene, and decatetraene.

Exemplary cyclic olefinyl groups include monoolefinyl groups such as cyclobutenyl, cyclopentenyl, methylcyclopentenyl, dimethylcyclopentenyl, cyclohexenyl, methylcyclohexenyl, dimethylcyclohexenyl, trimethylcyclohexenyl, tetramethylcyclohexenyl, cyclooctenyl, methylcyclooctenyl, dimethylcyclooctenyl, tetramethylcyclooctenyl, cyclodecenyl, and norbornyl; and cyclic polyenyl groups having at least two unsaturated groups in the molecule such as cyclobutadienyl, cyclohexadienyl, cyclooctadienyl, cyclooctatrienyl, cyclooctatetraenyl, cyclodecadienyl, cyclodecatrienyl, cyclodecatetraenyl, and norbornadienyl, exclusive of cyclopentadienyl.

Exemplary acyclic olefinyl groups include acyclic (chainlike) monoolefinyl groups such as vinyl, allyl, methallyl, butenyl, isobutenyl, pentenyl, hexenyl, octenyl, and decenyl; and acyclic (chainlike) polyenyl groups having at least two unsaturated groups in the molecule such as butadienyl, methylbutadienyl, dimethylbutadienyl, pentadienyl, methylpentadienyl, dimethylpentadienyl, hexadienyl, hexatrienyl, octadienyl, octatrienyl, octatetraenyl, decadienyl, decatrienyl, and decatetraenyl.

Each of the foregoing ligands may be partially substituted with a halogen atom selected from fluorine, chlorine, bromine and iodine; alkoxy group such as methoxy, ethoxy, propoxy, butoxy, pentoxy, hexoxy, octyloxy, or decyloxy; or haloalkyl group such as trifluoromethyl, pentafluoroethyl, trifluoropropyl, nonafluorobutyl, trichloromethyl or trichloropropyl.

Furthermore, one or more carbon atoms in the ligand X may be substituted by nitrogen, phosphorus, bismuth, silicon or germanium atoms.

The bonds between Fe and carbon atoms in ligands X may be solely covalent bonds, solely coordinate bonds, or both.

In particular, the iron complex of formula (1) is an iron complex in which Fe has only bonds with carbon atoms in ligands X, the total number of bonds is preferably 2 to 10, and every ligand X is a ligand having an unsaturated bond in the molecule.

Inter alia, the preferred iron complex is a binuclear complex in which ligand X is an aryl group and the total number of bonds of Fe with carbon atoms in ligands X is 2.

Also preferred are mononuclear complexes in which the total number of bonds of Fe with carbon atoms in ligands X is 6 to 10, more preferably 10.

Herein, ligand X is preferably selected from among cyclic olefin, acyclic olefin, cyclic olefinyl and acyclic olefinyl groups having 1 to 5 unsaturated groups in the molecule, more preferably from among cyclic polyene, acyclic polyene, cyclic polyenyl and acyclic polyenyl groups having at least 2 unsaturated groups in the molecule. Notably, at least 2 unsaturated groups in the molecule may be either continuous or discontinuous.

On the other hand, the two-electron ligand (L) is a ligand containing two electrons coordinating with Fe.

The two-electron ligand is not particularly limited and may be any of ligands commonly used as the two-electron ligand for metal complexes. Typical examples include carbon monoxide (carbonyl group); amine, imine, nitrogen-containing heterocyclic, phosphine, arsine, alcohol, thiol, ether, sulfide and carbene compounds containing a non-covalent electron pair (odd electron) such as nitrogen, phosphorus, oxygen or sulfur; and aldehyde, ketone, nitrile, and isocyanide compounds containing both odd electron and it electron. The foregoing compounds other than carbon monoxide are preferred, and the nitrogen-containing heterocyclic compounds, carbene compounds and isocyanide compounds are more preferred.

Suitable amine compounds include tertiary amine compounds of the formula: $R_3N$ wherein R is each independently an alkyl, aryl or aralkyl group, which may be substituted with a halogen atom, hydroxyl or alkoxy moiety. Examples of the halogen atom, alkyl, aryl and aralkyl groups are as exemplified above.

Preferred alkoxy groups are $C_1$-$C_{10}$ groups although the carbon count is not critical. Examples include methoxy, ethoxy, n-propoxy, i-propoxy, n-butoxy, i-butoxy, s-butoxy, t-butoxy, n-pentoxy, n-hexoxy, n-heptyloxy, n-octyloxy, n-nonyloxy, and n-decyloxy.

Suitable imine compounds include those of the formula: RC(=NR)R wherein R is each independently as defined above.

Exemplary phosphine compounds include those of the formula: $R_3P$ wherein R is each independently as defined above.

Exemplary arsine compounds include those of the formula: $R_3As$ wherein R is each independently as defined above.

Exemplary alcohol compounds include those of the formula: ROH wherein R is each independently as defined above.

Suitable thiol compounds include those corresponding to the above alcohol compounds wherein oxygen is replaced by sulfur.

Exemplary ether compounds include those of the formula: ROR wherein R is each independently as defined above.

Suitable sulfide compounds include those corresponding to the above ether compounds wherein oxygen is replaced by sulfur.

Exemplary ketone compounds include those of the formula: RCOR wherein R is each independently as defined above.

Exemplary nitrile compounds include those of the formula: RCN wherein R is each independently as defined above.

Preferred isocyanide compounds are those of the formula (2): Y—NC, but not limited thereto.

Herein Y is an optionally substituted $C_1$-$C_{30}$ monovalent organic group which may be separated by at least one atom selected from oxygen, nitrogen, sulfur and phosphorus.

The $C_1$-$C_{30}$ monovalent organic groups are preferably $C_1$-$C_{30}$ monovalent hydrocarbon groups, but not limited thereto.

Suitable monovalent hydrocarbon groups include alkyl, alkenyl, alkynyl, aryl and aralkyl groups. Examples of the alkyl, aryl and aralkyl groups are as exemplified above.

The alkenyl groups are preferably $C_2$-$C_{20}$ alkenyl groups. Examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

The alkynyl groups are preferably $C_2$-$C_{20}$ alkynyl groups. Examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, and n-1-pentadecynyl, and n-1-eicosynyl.

The $C_1$-$C_{30}$ monovalent organic group may have a substituent or a plurality of identical or different substituents at arbitrary positions.

Examples of the substituent include halogen atoms such as fluorine and chlorine, alkoxy groups such as methoxy, ethoxy and propoxy, and amino groups such as dialkylamino.

Examples of the isocyanide compound which may be preferably used herein as the ligand include, but are not limited to, alkyl isocyanides such as methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide, and 2-adamantyl isocyanide; aryl isocyanides such as phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide, and 2-methyl-1-naphthyl isocyanide; and aralkyl isocyanides such as benzyl isocyanide and phenylethyl isocyanide.

The carbene compounds are preferably those of the formula (3), but not limited thereto.

[Chemical Formula 3]

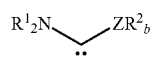

(3)

In formula (3), Z is a carbon, nitrogen or oxygen atom, b is 3 when Z is a carbon atom, b is 2 when Z is a nitrogen atom, b is 1 when Z is an oxygen atom.

$R^1$ and $R^2$ are each independently a $C_1$-$C_{30}$ alkyl, aryl or aralkyl group which may be substituted with a halogen atom or alkoxy group. Any one of $R^1$ and any one of $R^2$ may bond together to form a divalent organic group so that the compound has a cyclic structure. In this case, the cyclic structure may contain a nitrogen atom and/or unsaturated bond therein.

Examples of the halogen atom, $C_1$-$C_{30}$ alkyl, aryl and aralkyl groups, and alkoxy groups are as exemplified above.

Preferred are cyclic carbene compounds of the formula (4).

[Chemical Formula 4]

(4)

In formula (4), A is a $C_2$-$C_5$ divalent organic group which may contain a nitrogen atom and/or unsaturated bond. Exemplary groups include methylene, ethylene, propylene, trimethylene, n-butylene, isobutylene, s-butylene, vinylene, and prop-1-ene-1,3-diyl (propenylene).

Examples of the cyclic carbene compound are given below, but not limited thereto.

[Chemical Formula 5]

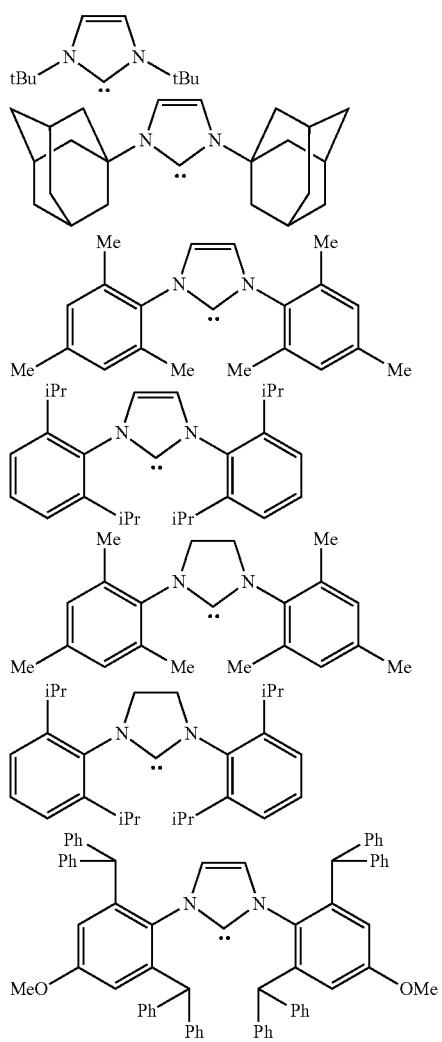

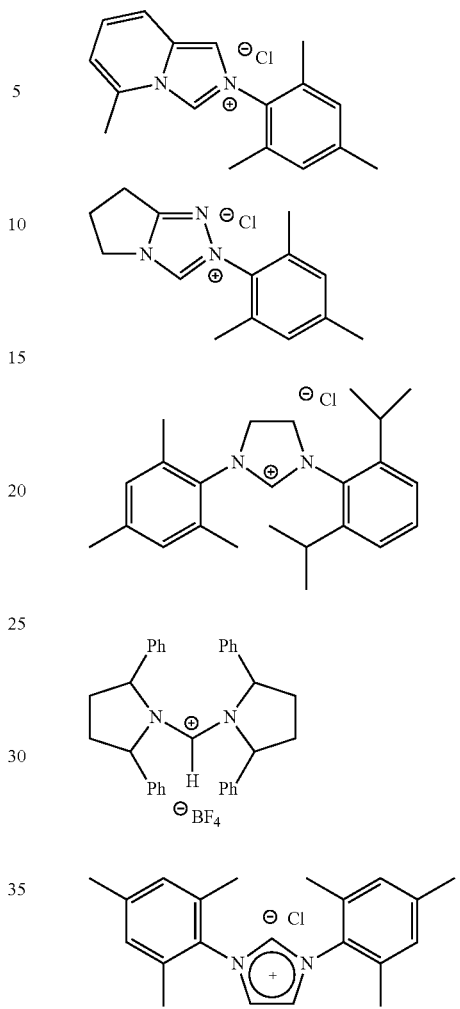

Besides, hydrosilylation reaction may be performed while an imidazolium salt as a precursor is reacted with a base such as KOtBu to generate a carbene compound in the system.

Examples of the imidazolium salt as a precursor include the following compounds, but are not limited thereto.

[Chemical Formula 6]

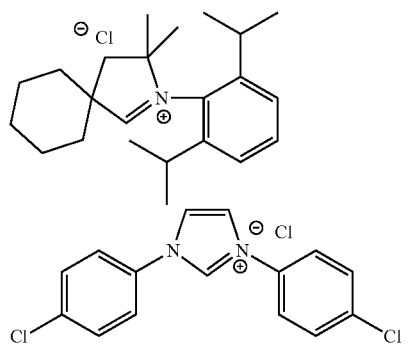

Examples of the nitrogen-containing heterocyclic compound include pyrrole, imidazole, pyridine, terpyridine, bisiminopyridine, pyrimidine, oxazoline, and isooxazoline compounds. Especially preferred are bisiminopyridine compounds of the formula (5) and terpyridine compounds of the formula (6).

[Chemical Formula 7]

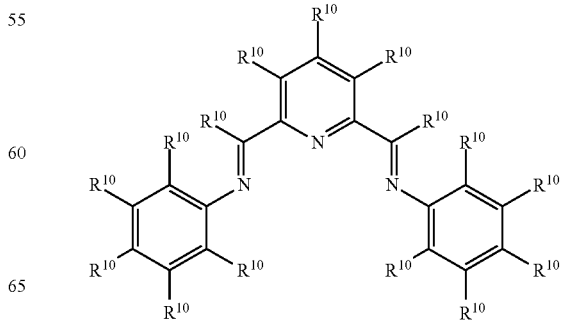

(5)

-continued

[Chemical Formula 8]

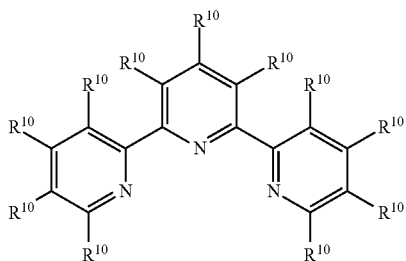

(6)

Herein $R^{10}$ is each independently hydrogen or an optionally substituted $C_1$-$C_{10}$ alkyl group. Suitable alkyl groups are as exemplified above.

Examples of the bisiminopyridine compound include 2,6-bis[1-(2,6-dimethylphenylimino)ethyl]pyridine, 2,6-bis[1-(2,6-diethylphenylimino)ethyl]pyridine, and 2,6-bis[1-(2,6-diisopropylphenylimino)ethyl]pyridine.

Typical of the terpyridine compound is 2,2':6',2"-terpyridine.

In preparing the inventive hydrosilylation iron catalyst, the amounts of the iron complex as precursor and the two-electron ligand used are not particularly limited. Preferably the two-electron ligand is used in an amount of about 0.5 to 10 equivalents, more preferably 1 to 6 equivalents, and even more preferably 1 to 3 equivalents per equivalent of the iron complex.

When hydrosilylation reaction is carried out in the presence of the inventive hydrosilylation iron catalyst, the amount of the catalyst used is not particularly limited. In order that the reaction take place under mild conditions of the order of room temperature to 100° C. to form the desired product in high yields, the catalyst is preferably used in an amount of at least 0.1 mol %, more preferably at least 0.5 mol % of metal compound per mole of the substrate, aliphatic unsaturated bond-containing compound.

Although no upper limit is imposed on the amount of metal compound used, the upper limit is preferably about 10 mol %, more preferably 5 mol % per mole of the substrate, as viewed from the economic standpoint.

The inventive hydrosilylation iron catalyst may be used after isolation from an iron complex catalyst prepared from the iron complex as precursor and the two-electron ligand. In an alternative embodiment, the catalyst may be prepared from the iron complex as precursor and the two-electron ligand in situ in a system where hydrosilylation reaction of a compound having an aliphatic unsaturated bond with a hydrosilane compound having a Si—H group or organohydropolysiloxane compound is carried out. The latter embodiment wherein the catalyst is prepared in situ and used without isolation is preferable from the standpoint of convenience of operation.

In this embodiment, once the catalyst is prepared from the iron complex as precursor and the two-electron ligand, the compound having an aliphatic unsaturated bond and the hydrosilane compound having a Si—H group or organohydropolysiloxane compound may be added thereto, or separate sets of some components may be fed, or all components may be fed at a time.

Although the reaction conditions for the iron complex as precursor and the two-electron ligand are not particularly limited, generally the reaction temperature is about 10 to about 100° C., preferably 20 to 80° C. and the reaction time is about 1 to about 48 hours.

Although an organic solvent may be used during catalyst preparation and hydrosilylation reaction, the invention favors a solventless or neat system.

The organic solvent, if used, may be of any type as long as the reaction is not affected. Examples include aliphatic hydrocarbons such as pentane, hexane, heptane, octane, and cyclohexane, ethers such as diethyl ether, diisopropyl ether, dibutyl ether, cyclopentyl methyl ether, tetrahydrofuran and 1,4-dioxane; and aromatic hydrocarbons such as benzene, toluene, xylene, and mesitylene.

In conducting hydrosilylation reaction using the inventive hydrosilylation iron catalyst, as long as a compound having an aliphatic unsaturated bond such as an olefin, silane or organopolysiloxane compound having an aliphatic unsaturated bond and a silane or organopolysiloxane compound having a Si—H bond are used in combination, no limit is imposed on the structure of the respective compounds.

The hydrosilylation reaction using the inventive hydrosilylation iron catalyst is applicable to all applications which are industrially implemented using prior art platinum catalysts, including silane coupling agents obtained from an olefin compound having an aliphatic unsaturated bond and a silane compound having a Si—H bond, and modified silicone oils obtained from an olefin compound having an aliphatic unsaturated bond and an organopolysiloxane having a Si—H bond, as well as silicone cured products obtained from an organopolysiloxane compound having an aliphatic unsaturated bond and an organopolysiloxane having a Si—H bond.

EXAMPLES

Synthesis Examples, Examples and Comparative Examples are given below by way of illustration and not by way of limitation.

For the synthesis of metal complexes, all operations were carried out in nitrogen or argon atmosphere using the Schlenk tube technique or glove box. All solvents were deoxygenated and dehydrated by well-known methods before they were used in the preparation of metal compounds.

Hydrosilylation reaction and solvent purification of alkenes were always carried out in an inert gas atmosphere. The solvents and other ingredients were purified, dried and deoxygenated by well-known methods before they were used in various reactions.

Analyses of $^1$H and $^{13}$C-NMR spectroscopy were performed by JNM-ECA 600 and JNM-LA 400 of JEOL Ltd., IR spectroscopy by FT/IR-550 of JASCO Corp., elemental analysis by 2400II/CHN of Perkin Elmer, x-ray crystallography analysis by VariMax (MoK α-ray 0.71069 angstrom) of Rigaku Corp.

It is understood that hydrogen atoms are omitted from the chemical structural formula, shown below, according to the conventional expression. NHC stands for N-heterocyclic carbene.

(1) Synthesis of Metal Compounds

[Synthesis Example 1] Synthesis of [(Fe(mesityl)(μ-mesityl)]$_2$

With reference to Organometallics, 1993, 12, 2414, the compound was synthesized by the following procedure.

A 50 mL two-neck recovery flask was charged with 1.08 g (44.3 mmol) of magnesium ribbon and 35 mL of THF, after which 8.49 g (42.6 mmol) of bromomesitylene was slowly added dropwise. It was confirmed that exotherm ceased at the end of dropwise addition, after which the reaction solution was stirred at 60° C. for 3 hours. The solution was filtered through a glass filter, obtaining a THF solution of mesitylmagnesium bromide Grignard reagent.

A 100 mL Schlenk flask was charged with 2.63 g (20.7 mmol) of $FeCl_2$, 30 mL of THF, and 10 mL of 1,4-dioxane and cooled down to −78° C. The THF solution of mesitylmagnesium bromide Grignard reagent was slowly added to the flask, followed by stirring at 25° C. for 2 hours. On this occasion, the reaction solution turned from a brown suspension to a red suspension. Thereafter, the precipitated solid was separated by centrifugation and dried in vacuum. The resulting red solid was dissolved in diethyl ether, after which the solid was separated again by centrifugation and recrystallized at −30° C., obtaining a crystal (4.36 g, yield 72%). The crystal was identified by $^1$H-NMR analysis in $C_6D_6$.

$^1$H-NMR (600 MHz, $C_6D_6$) δ: 23.68 (s, 2H), 23.17 (s, 2H), 21.44 (s, 3H), 17.94 (s, 3H), 10.19 (s, 6H), −6.66 (s, 6H)

[Synthesis Example 2] Synthesis of Iron Biscyclooctatetraene

With reference to Non-Patent Document (Inorganic Syntheses, 1974, 15, 2), iron biscyclooctatetraene was synthesized by the following procedure.

A 100 mL Schlenk flask was charged with 1.0 g (2.9 mmol) of iron triacetylacetonate, 20 mL of diethyl ether, and 2.0 g (19.3 mmol) of cyclooctatetraene. The mixture was cooled down to −78° C., to which 10 mL (1.0 M) of hexane solution of triethylaluminum was slowly added dropwise. After the addition of the entire amount, the solution was stirred at −10° C. for 2 hours. The solution was stirred at room temperature for 30 minutes, cooled down to −78° C. again, and held for 3 hours, allowing a crystal to precipitate out. With the supernatant removed, the resulting crystal was dissolved in diethyl ether again and recrystallized at −30° C., obtaining iron biscyclooctatetraene (abbreviated as $Fe(COT)_2$, hereinafter) in black crystal form (0.47 g, yield 62%). The crystal was identified by $^1$H-NMR analysis in $C_6D_6$.

$^1$H-NMR (600 MHz, $C_6D_6$) δ: 5.05 (s, 16H)

[Synthesis Example 3] Synthesis of Iron bis(3-methylpentadienyl)

With reference to Non-Patent Document (Organometallics, 1983, 2, 1220-1228, iron bis(3-methylpentadienyl) was synthesized by the following procedure.

A 50 mL two-neck recovery flask was charged with 1.37 g (12.2 mmol) of potassium t-butoxide, 20 mL of hexane, and 7.3 mL (12.2 mmol) of a hexane solution of 1.67M n-butyl lithium, followed by stirring. To the flask, 1.05 g (12.8 mmol) of 3-methylpentadiene was added, followed by stirring at room temperature for 1 hour. The reaction solution turned from white to red while a precipitate formed. With the supernatant removed, the residue was washed with hexane and dried in vacuum. This was dissolved in 20 mL of THF, obtaining a THF solution of 3-methylpentadienylpotassium.

A 50 mL Schlenk flask was charged with 0.78 g (6.2 mmol) of $FeCl_2$ and 5 mL of THF, and cooled down to −78° C. To the flask, the THF solution of 3-methylpentadienylpotassium was slowly added dropwise. At the end of dropwise addition, the solution was stirred at room temperature for 16 hours. The reaction product was vacuum dried, dissolved in pentane, filtered through Celite, and recrystallized at −78° C. The resulting red solid was purified by sublimation at 50° C. in vacuum, obtaining iron bis(3-methylpentadienyl) (abbreviated as $(MPDE)_2Fe$, hereinafter) in red solid form (0.10 g, yield 8%). The solid was identified by $^1$H-NMR analysis in $C_6D_6$.

$^1$H-NMR (600 MHz, $C_6D_6$) δ: 0.34 (d, J=9.6 Hz, 4H), 1.69 (s, 6H), 2.87 (d, J=8.2 Hz, 4H), 3.80 (t, J=9.6 Hz, 4H)

[Synthesis Example 4] Synthesis of Iron bis(2,4-dimethylpentadienyl)

With reference to Non-Patent Document (Organometallics, 1983, 2, 1220-1228, iron bis(2,4-dimethylpentadienyl) was synthesized by the following procedure.

A 50 mL two-neck recovery flask was charged with 1.19 g (10.6 mmol) of potassium t-butoxide, 5 mL of hexane, and 6.5 mL (10.9 mmol) of a hexane solution of 1.67M n-butyl lithium, followed by stirring. To the flask, 1.00 g (10.4 mmol) of 2,4-dimethylpentadiene was added, followed by stirring at room temperature for 1 hour. The reaction solution turned from white to red while a precipitate formed. With the supernatant removed, the residue was washed with hexane and dried in vacuum. This was dissolved in 20 mL of THF, obtaining a THF solution of 2,4-dimethylpentadienylpotassium.

A 50 mL Schlenk flask was charged with 0.63 g (5.0 mmol) of $FeCl_2$ and 5 mL of THF, and cooled down to −78° C. To the flask, the THF solution of 2,4-dimethylpentadienylpotassium was slowly added dropwise. At the end of dropwise addition, the solution was stirred at room temperature for 21 hours. The reaction product was vacuum dried, dissolved in pentane, filtered through Celite, and recrystallized at −78° C. The resulting red solid was purified by sublimation at 50° C. in vacuum, obtaining iron bis(2,4-dimethylpentadienyl) (abbreviated as $(DMPDE)_2Fe$, hereinafter) in red solid form (0.30 g, yield 25%). The solid was identified by $^1$H-NMR analysis in $C_6D_6$.

$^1$H-NMR (600 MHz, $C_6D_6$) δ: 0.28 (br, 4H), 1.82 (br, 12H), 2.65 (br, 4H), 4.35 (br, 2H)

[Synthesis Example 5] Synthesis of Iron Complex A

Figure 2:
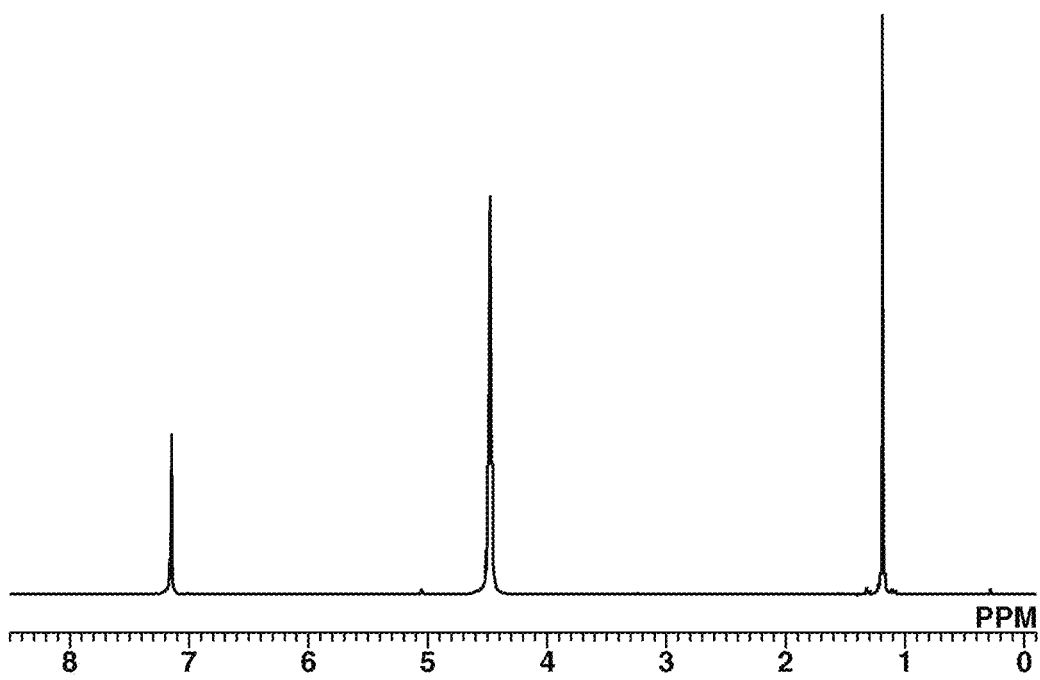
FIG. 2 is a diagram of the $^1$H-NMR spectrum of iron complex A in Synthesis Example 5.
Figure 3:
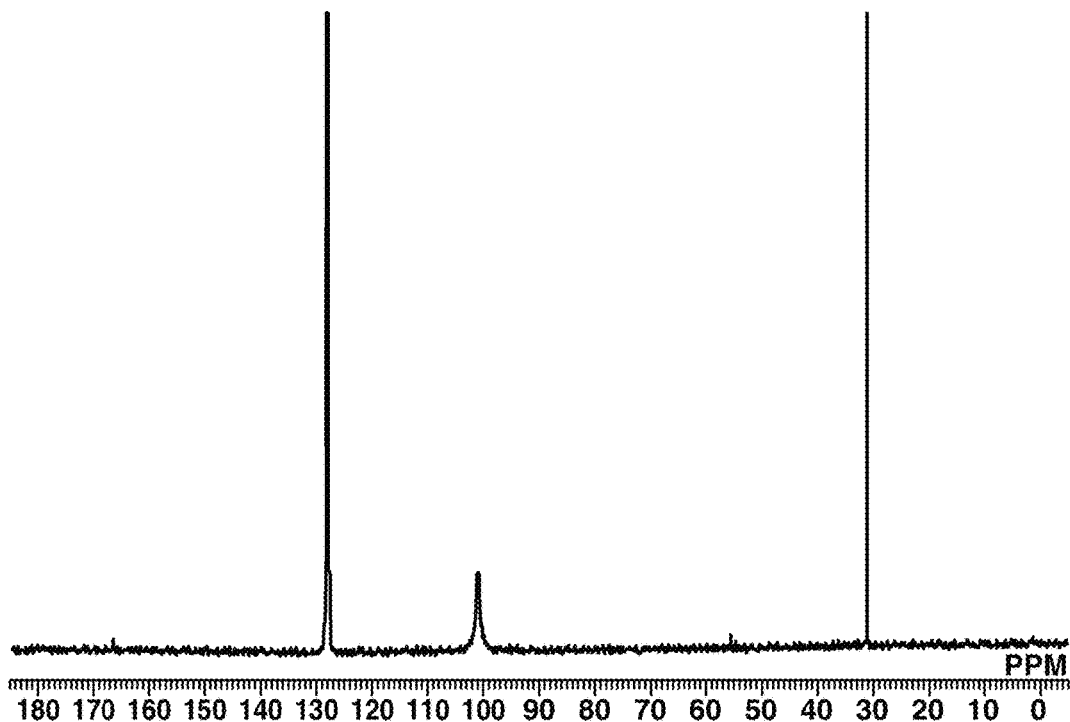
FIG. 3 is a diagram of the $^{13}$C-NMR spectrum of iron complex A in Synthesis Example 5.

A 20 mL Schlenk flask was charged with 17 mg (0.07 mmol) of $Fe(COT)_2$, 12 mL of pentane, and 7 mg (0.08 mmol) of t-butyl isocyanide (abbreviated as tBuNC, hereinafter), followed by stirring at room temperature for 8 hours. Thereafter, the solution was filtered and the residue was recrystallized at −30° C., obtaining a black crystal (11 mg, yield 48%). The crystal was identified by x-ray crystallography analysis, elemental analysis and NMR spectroscopy. FIG. 1 shows the structure of the resulting Iron complex A, FIG. 2 shows the data of $^1$H-NMR spectroscopy, and FIG. 3 shows the data of $^{13}$C-NMR spectroscopy.

$^1$H-NMR (600 MHz, $C_6D_6$) δ: 1.19 (s, 9H), 4.48 (br, 16H)
$^{13}$C-NMR (151 MHz, $C_6D_6$) δ: 31.1, 55.6, 100.9 (br), 166.5

[Synthesis Example 6] Synthesis of Iron Complex B

Figure 4:
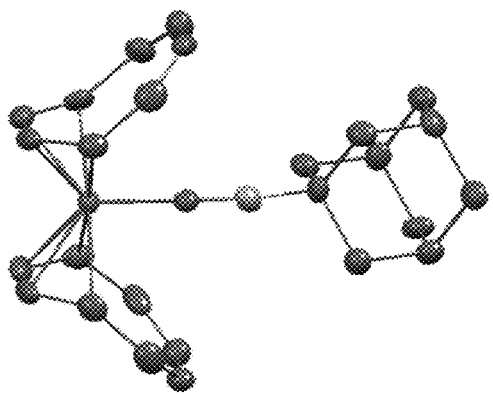
FIG. 4 is a model showing the results of x-ray crystallographic analysis on iron complex B obtained in Synthesis Example 6.
Figure 5:
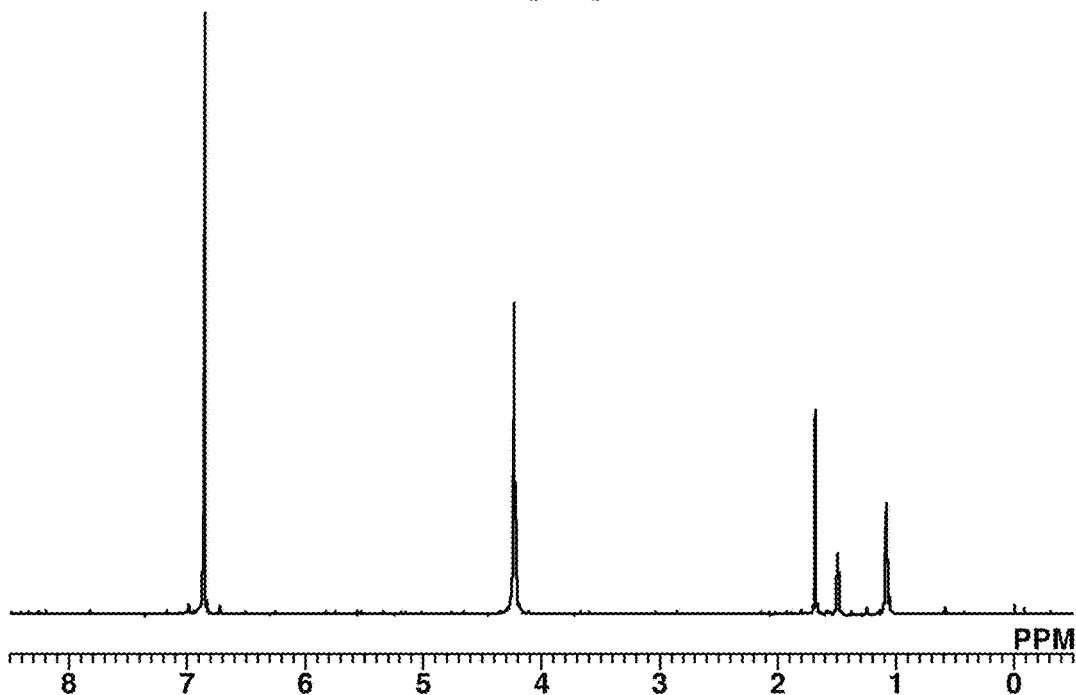
FIG. 5 is a diagram of the $^1$H-NMR spectrum of iron complex B in Synthesis Example 6.
Figure 6:
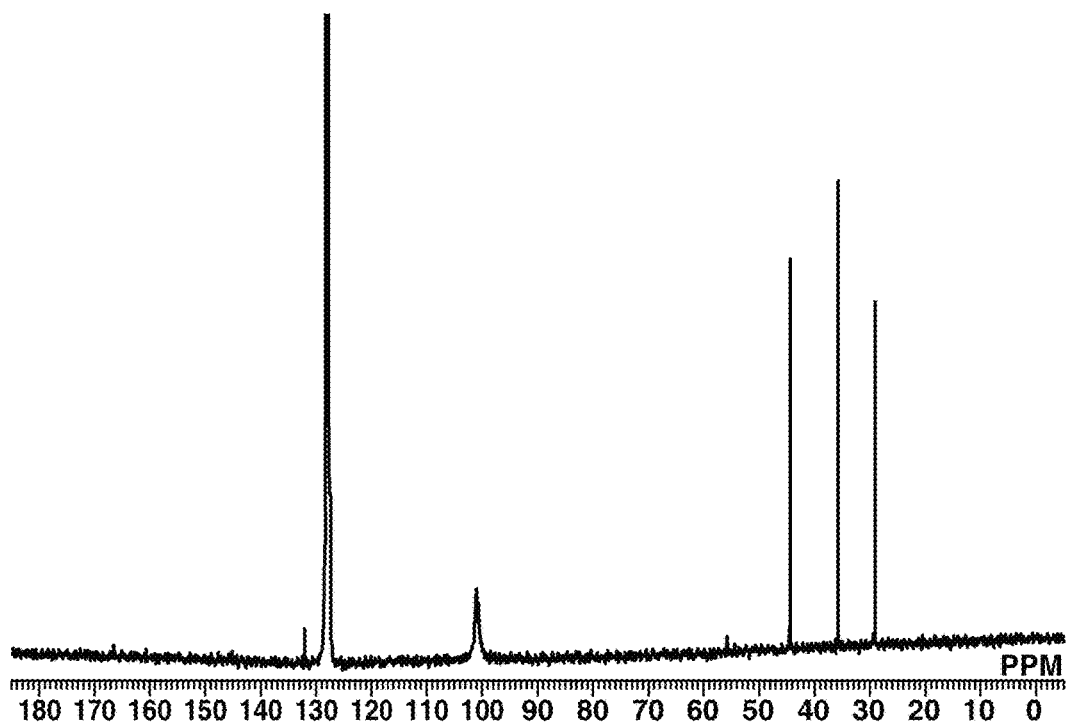
FIG. 6 is a diagram of the $^{13}$C-NMR spectrum of iron complex B in Synthesis Example 6.

A 20 mL Schlenk flask was charged with 50 mg (0.19 mmol) of $Fe(COT)_2$, 2 mL of toluene, and 33 mg (0.21 mmol) of 1-isocyanoadamantane (abbreviated as AdNC, hereinafter), followed by stirring at room temperature for 1 hour. Thereafter, the solution was filtered. Pentane was added to the residue, which was recrystallized at −30° C., obtaining a black crystal (50 mg, yield 62%). The crystal was identified by x-ray crystallography analysis, elemental analysis and NMR spectroscopy. FIG. 4 shows the structure of the resulting Iron complex B, FIG. 5 shows the data of $^1$H-NMR spectroscopy, and FIG. 6 shows the data of $^{13}$C-NMR spectroscopy.

$^1$H-NMR (600 MHz, C$_6$D$_6$) δ: 1.37 (br, 6H), 1.79 (s, 3H), 1.97 (s, 6H), 4.52 (br, 16H)

$^{13}$C-NMR (151 MHz, C$_6$D$_6$) δ: 29.3, 35.8, 44.4, 55.7, 101.0 (br), 166.6

[Synthesis Example 7] Synthesis of Iron Complex C

Figure 7:
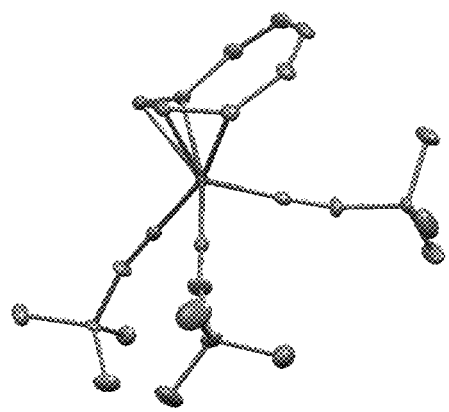
FIG. 7 is a model showing the results of x-ray crystallographic analysis on iron complex C obtained in Synthesis Example 7.
Figure 8:
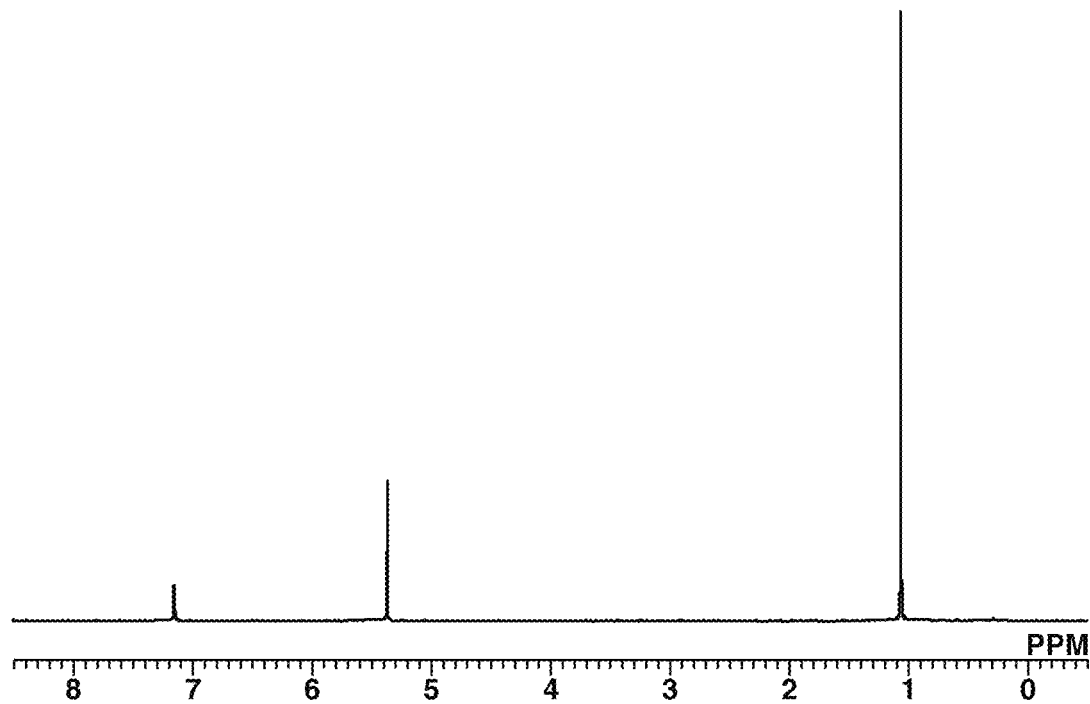
FIG. 8 is a diagram of the $^1$H-NMR spectrum of iron complex C in Synthesis Example 7.
Figure 9:
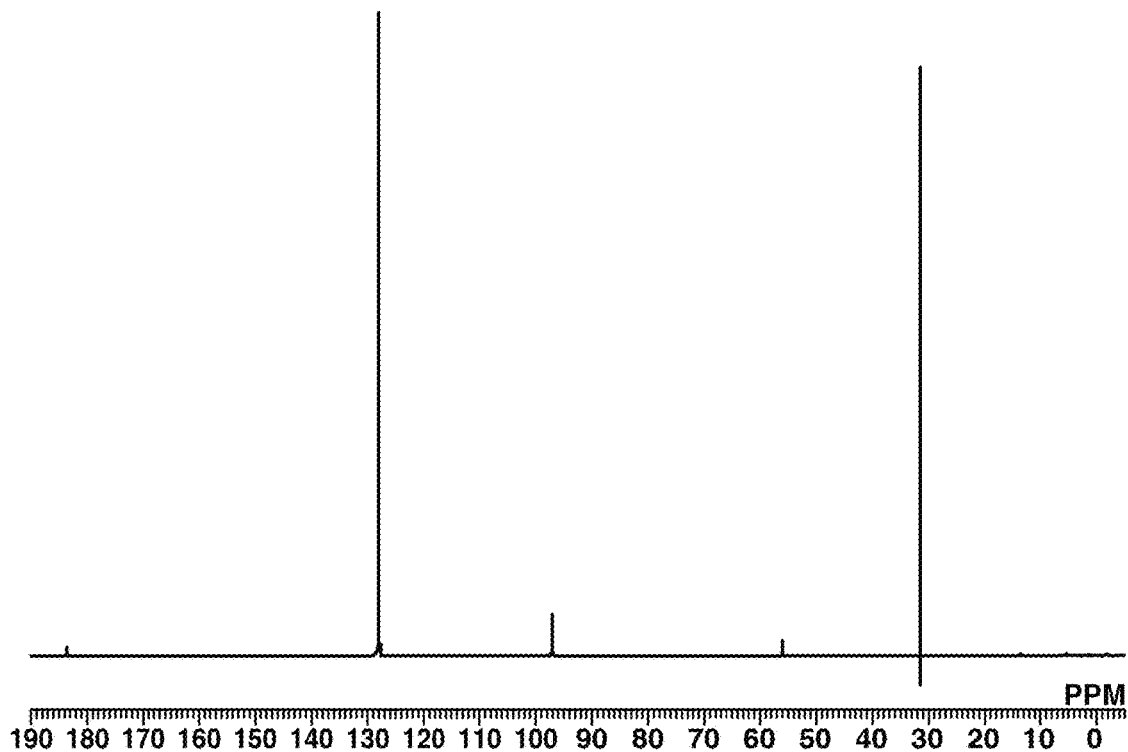
FIG. 9 is a diagram of the $^{13}$C-NMR spectrum of iron complex C in Synthesis Example 7.

A 20 mL Schlenk flask was charged with 42 mg (0.16 mmol) of Fe(COT)$_2$, 4 mL of pentane, and 54 mg (0.65 mmol) of tBuNC, followed by stirring at room temperature for 8 hours. Thereafter, the solution was filtered and the residue was recrystallized at −30° C., obtaining a red crystal (32 mg, yield 50%). The crystal was identified by x-ray crystallography analysis, elemental analysis and NMR spectroscopy. FIG. 7 shows the structure of the resulting Iron complex C, FIG. 8 shows the data of $^1$H-NMR spectroscopy, and FIG. 9 shows the data of $^{13}$C-NMR spectroscopy.

$^1$H-NMR (600 MHz, C$_6$D$_6$) δ: 1.07 (s, 27H), 5.37 (br, 8H)

$^{13}$C-NMR (151 MHz, C$_6$D$_6$) δ: 31.5, 55.9, 97.0 (br), 183.6

[Synthesis Example 8] Synthesis of Iron Complex D

Figure 10:
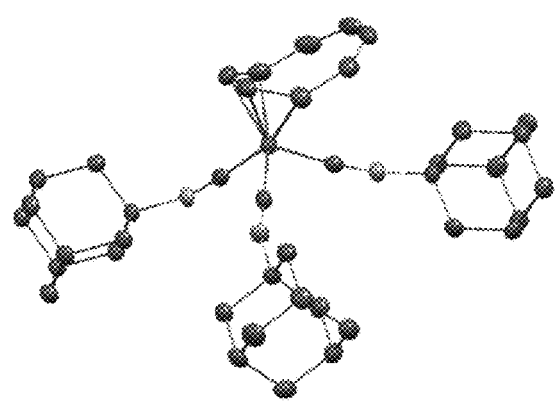
FIG. 10 is a model showing the results of x-ray crystallographic analysis on iron complex D obtained in Synthesis Example 8.
Figure 11:
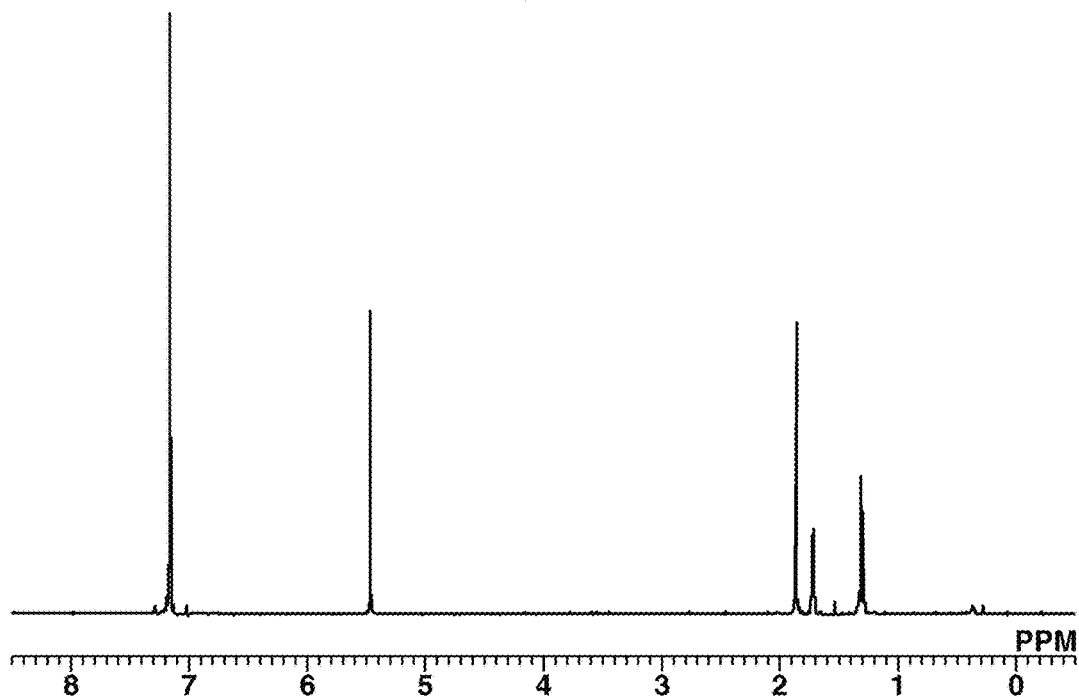
FIG. 11 is a diagram of the $^1$H-NMR spectrum of iron complex D in Synthesis Example 8.
Figure 12:
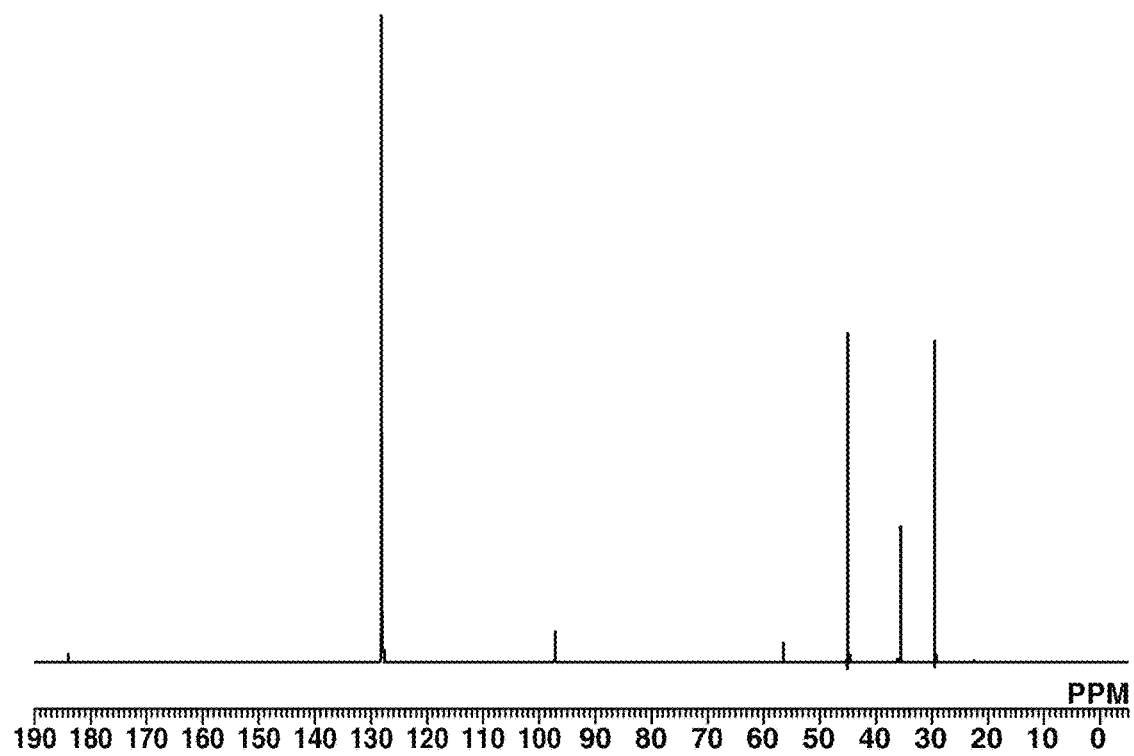
FIG. 12 is a diagram of the $^{13}$C-NMR spectrum of iron complex D in Synthesis Example 8.

A 20 mL Schlenk flask was charged with 100 mg (0.38 mmol) of Fe(COT)$_2$, 4 mL of toluene, and 185 mg (1.15 mmol) of AdNC, followed by stirring at room temperature for 1 hour. Thereafter, the solution was filtered, and the residue was combined with pentane and recrystallized at −30° C., obtaining a red crystal (168 mg, yield 62%). The crystal was identified by x-ray crystallography analysis, elemental analysis and NMR spectroscopy. FIG. 10 shows the structure of the resulting Iron complex D, FIG. 11 shows the data of $^1$H-NMR spectroscopy, and FIG. 12 shows the data of $^{13}$C-NMR spectroscopy.

$^1$H-NMR (600 MHz, C$_6$D$_6$) δ: 1.32 (br, 18H), 1.72 (s, 9H), 1.86 (s, 18H), 5.46 (br, 8H)

$^{13}$C-NMR (151 MHz, C$_6$D$_6$) δ: 29.5, 35.8, 45.1, 56.4, 97.1, 183.8

(2) Hydrosilylation of 1-Octene with 1,1,3,3,3-Pentamethyldisiloxane Using Various Isocyanide Ligands

[Chemical Formula 9]

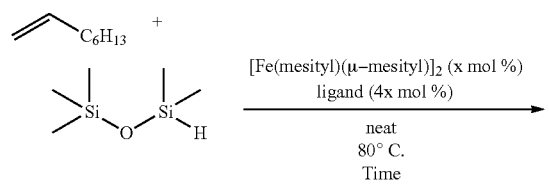

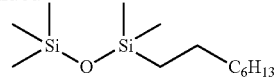

[Example 1] Hydrosilylation of 1-Octene with 1,1,3,3,3-Pentamethyldisiloxane Using Isocyanide Ligand A screw-top vial was charged with 15 mg (0.025 mmol) of [Fe(mesityl) (μ-mesityl)]$_2$ in Synthesis Example 1, 11 μL (0.10 mmol) of tBuNC, 98 μL (0.5 mmol) of 1,1,3,3,3-pentamethyldisiloxane, and 78 μL (0.5 mmol) of 1-octene. The vial was closed, after which the contents were stirred at 80° C. for 16 hours.

After cooling, 1.0 mmol of anisole as an internal standard was added to the reaction solution and stirred. A minute amount of the solution was dissolved in deuterochloroform, passed through an alumina column to remove the catalyst, and analyzed by $^1$H-NMR spectroscopy to determine the structure and yield of the product. It is noted that in the following Examples, a test sample was prepared according to the same procedure and analyzed by $^1$H-NMR spectroscopy. As a result, it was confirmed that the signal assigned to the ethylene site of 1-octene as the reactant disappeared completely. Instead, a multiplet near 0.50 ppm indicative of the signal assigned to proton on silicon-adjoining carbon in the desired product, 1,1,1,3,3-pentamethyl-3-octyldisiloxane was observed, from which a yield was determined. The results are shown in Table 1.

$^1$H-NMR (396 MHz, CDCl$_3$) δ: 0.03 (s, 6H), 0.06 (s, 9H), 0.50 (t, J=7.7 Hz, 2H), 0.88 (t, J=6.8 Hz, 3H), 1.19-1.34 (br, 12H)

[Example 2] Hydrosilylation of 1-Octene with 1,1,3,3,3-Pentamethyldisiloxane Using NHC Ligand A screw-top vial was charged with 8 mg (0.015 mmol) of [Fe(mesityl) (μ-mesityl)]$_2$ in Synthesis Example 1, 18 mg (0.06 mmol) of 1,3-dimesitylimidazol-2-ylidene, 254 μL (1.3 mmol) of 1,1,3,3,3-pentamethyldisiloxane, and 157 μL (1.0 mmol) of 1-octene. The vial was closed, after which the contents were stirred at 80° C. for 24 hours.

After cooling, analysis was made by $^1$H-NMR spectroscopy to determine the structure and yield of the product. As a result, it was confirmed that the signal assigned to the reactant disappeared completely. Instead, a multiplet near 0.50 ppm indicative of the signal assigned to the desired product was observed, from which a yield was determined. The results are shown in Table 1.

TABLE 1

| | Catalyst precursor amount (mol %) | Ligand | Reaction time (h) | Conversion (%) | Yield (%) |
|---|---|---|---|---|---|
| Example 1 | 5 | tBuNC | 16 | >99 | >99 |
| Example 2 | 1.5 | 1,3-dimesitylimidazol-2-ylidene | 24 | >99 | 15 |

(3) Hydrosilylation 1 of Styrene with 1,1,3,3,3-Pentamethyldisiloxane Using Isocyanide Ligand

[Chemical Formula 10]

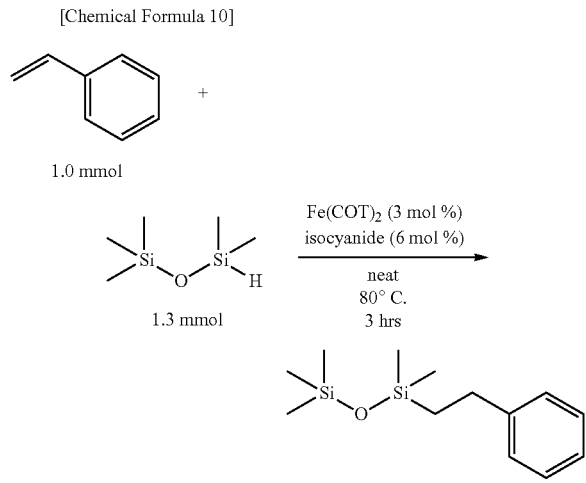

Examples 3 to 10

A screw-top vial was charged with 8 mg (0.03 mmol) of Fe(COT)$_2$ in Synthesis Example 2, 0.06 mmol of an isocyanide listed in Table 2, 254 μL (1.3 mmol) of 1,1,3,3,3-pentamethyldisiloxane and 115 μL (1.0 mmol) of styrene. The vial was closed, after which the contents were stirred at 80° C. for 3 hours. After cooling, analysis was made by $^1$H-NMR spectroscopy to determine the structure and yield of the product. As a result, it was confirmed that the signal assigned to the reactant disappeared completely. Instead, a multiplet near 0.89 ppm indicative of the signal assigned to proton on silicon-adjoining carbon in the desired product, 1,1,1,3,3-pentamethyl-3-phenethyldisiloxane was observed, from which a yield was determined. The results are shown in Table 2.

$^1$H-NMR (396 MHz, CDCl$_3$) δ: 0.07 (s, 6H), 0.09 (s, 9H), 0.86-0.92 (m, 2H), 2.61-2.68 (m, 2H), 7.13-7.33 (m, 5H)

TABLE 2

| | Isocyanide ligand | Conversion (%) | Yield (%) |
|---|---|---|---|
| Example 3 | tBuNC | >99 | 73 |
| Example 4 | AdNC | >99 | 74 |
| Example 5 | n-butyl isocyanide | >99 | 73 |
| Example 6 | isopropyl isocyanide | 79 | 57 |
| Example 7 | cyclohexyl isocyanide | >99 | 75 |
| Example 8 | 1,1,3,3-tetramethylbutyl isocyanide | 56 | 11 |
| Example 9 | benzyl isocyanide | 18 | 6 |
| Example 10 | 2,6-diisopropylphenyl isocyanide | 62 | 7 |

(4) Hydrosilylation 1 of Various Alkenes with 1,1,3,3,3-Pentamethyldisiloxane Using tBuNC Ligand

[Chemical Formula 11]

[Example 11] Hydrosilylation of Styrene with 1,1,3,3,3-Pentamethyldisiloxane (Change of Reaction Conditions from Example 3)

A screw-top vial was charged with 8 mg (0.03 mmol) of Fe(COT)$_2$ in Synthesis Example 2, 7 μL (0.06 mmol) of tBuNC, 254 μL (1.3 mmol) of 1,1,3,3,3-pentamethyldisiloxane and 115 μL (1.0 mmol) of styrene. The vial was closed, after which the contents were stirred at 50° C. for 23 hours. After cooling, analysis was made by $^1$H-NMR spectroscopy to determine the structure and yield of the product. As a result, it was confirmed that the signal assigned to the reactant disappeared completely. Instead, a multiplet near 0.89 ppm indicative of the signal assigned to the desired product was observed, from which a yield was determined. The results are shown in Table 3.

[Example 12] Hydrosilylation of 4-Methoxystyrene with 1,1,3,3,3-Pentamethyldisiloxane Reaction was carried out according to the same procedure as in Example 11 aside from using 134 μL (1.0 mmol) of 4-methoxystyrene instead of styrene. As a result, it was confirmed that the signal assigned to the ethylene site of 4-methoxystyrene as the reactant disappeared completely. Instead, a multiplet at 0.89 ppm indicative of the signal assigned to proton on silicon-adjoining carbon in the desired product, 1-(4-methoxyphenylethyl)-1,1,3,3,3-pentamethyldisiloxane was observed, from which a yield was determined. The results are shown in Table 3.

$^1$H-NMR (396 MHz, CDCl$_3$) δ: 0.06 (s, 6H), 0.08 (s, 9H), 0.83-0.89 (m, 2H), 2.56-2.62 (m, 2H), 3.79 (s, 3H), 6.82 (d, J=8.2 Hz, 2H), 7.12 (d, J=8.2 Hz, 2H)

[Example 13] Hydrosilylation of 4-t-Butylstyrene with 1,1,3,3,3-Pentamethyldisiloxane Reaction was carried out according to the same procedure as in Example 11 aside from using 180 μL (1.0 mmol) of 4-t-butylstyrene instead of styrene. As a result, it was confirmed that the signal assigned to the ethylene site of 4-t-butylstyrene as the reactant disappeared completely. Instead, a multiplet near 0.89 ppm indicative of the signal assigned to proton on silicon-adjoining carbon in the desired product was observed, from which a yield was determined. The results are shown in Table 3.

Thereafter, the reaction solution was purified by silica gel column chromatography (developing solvent, hexane/ethyl acetate=10/1 by volume), obtaining 1-(4-(t-butyl)phenyl-ethyl)-1,1,3,3,3-pentamethyldisiloxane (302 mg, isolation yield 99%).

$^1$H-NMR (396 MHz, CDCl$_3$) δ: 0.08 (s, 6H), 0.08 (s, 9H), 0.85-0.92 (m, 2H), 2.58-2.65 (m, 2H), 7.10-7.16 (m, 2H), 7.21-7.29 (m, 2H)

$^{13}$C-NMR (99 MHz, CDCl$_3$) δ: 0.5, 2.1, 20.5, 29.0, 128.5, 129.3, 131.3, 143.8

[Example 14] Hydrosilylation of 4-Chlorostyrene with 1,1,3,3,3-Pentamethyldisiloxane Reaction was carried out according to the same procedure as in Example 11 aside from using 127 μL (1.0 mmol) of 4-chlorostyrene instead of styrene. As a result, it was confirmed that the signal assigned to the ethylene site of 4-chlorostyrene as the reactant disappeared completely. Instead, a multiplet at 0.89 ppm indicative of the signal assigned to proton on silicon-adjoining carbon in the desired product was observed, from which a yield was determined. The results are shown in Table 3.

Thereafter, the reaction solution was purified by silica gel column chromatography (developing solvent, hexane), obtaining 1-(4-chlorophenylethyl)-1,1,3,3,3-pentamethyldisiloxane (246 mg, isolation yield 86%).

$^1$H-NMR (396 MHz, CDCl$_3$) δ: 0.07 (s, 6H), 0.08 (s, 9H), 0.82-0.88 (m, 2H), 1.31 (s, 9H), 2.58-2.64 (m, 2H), 7.12-7.16 (m, 2H), 7.29-7.32 (m, 2H)

$^{13}$C-NMR (99 MHz, CDCl$_3$) δ: 0.4, 2.2, 20.4, 28.9, 31.6, 34.5, 125.3, 127.6, 142.3, 148.4

[Example 15] Hydrosilylation of 4-Fluorostyrene with 1,1,3,3,3-Pentamethyldisiloxane Reaction was carried out according to the same procedure as in Example 11 aside from using 119 μL (1.0 mmol) of 4-fluorostyrene instead of styrene. As a result, it was confirmed that the signal assigned to the ethylene site of 4-fluorostyrene as the reactant disappeared completely. Instead, a multiplet at 0.89 ppm indicative of the signal assigned to proton on silicon-adjoining carbon in the desired product was observed, from which a yield was determined. The results are shown in Table 3.

Thereafter, the reaction solution was purified by silica gel column chromatography (developing solvent, hexane/ethyl acetate=10/1 by volume), obtaining 1-(4-fluorophenyl-ethyl)-1,1,3,3,3-pentamethyldisiloxane (241 mg, isolation yield 89%).

$^1$H-NMR (396 MHz, CDCl$_3$) δ: 0.07 (s, 6H), 0.08 (s, 9H), 0.83-0.89 (m, 2H), 2.59-2.65 (m, 2H), 6.92-6.98 (m, 2H), 7.12-7.17 (m, 2H)

$^{13}$C-NMR (99 MHz, CDCl$_3$) δ: 0.5, 2.2, 20.7, 28.8, 115.0, 115.2, 129.2, 129.2, 140.9, 140.9, 160.0, 162.5

[Example 16] Hydrosilylation of Ethyl 4-Vinylbenzoate with 1,1,3,3,3-Pentamethyldisiloxane Reaction was carried out according to the same procedure as in Example 11 aside from using 176 mg (1.0 mmol) of ethyl 4-vinylbenzoate instead of styrene. As a result, it was confirmed that the signal assigned to the ethylene site of ethyl 4-vinylbenzoate as the reactant disappeared completely. Instead, a multiplet at 0.89 ppm indicative of the signal assigned to proton on silicon-adjoining carbon in the desired product was observed, from which a yield was determined. The results are shown in Table 3.

Thereafter, the reaction solution was purified by silica gel column chromatography (developing solvent, hexane/ethyl acetate=30/1 by volume), obtaining ethyl 2-(1,1,1,3,3-pentamethyldisiloxanyl)ethyl-4-benzoate (313 mg, isolation yield 96%).

$^1$H-NMR (396 MHz, CDCl$_3$) δ: 0.08 (s, 6H), 0.08 (s, 9H), 0.84-0.91 (m, 2H), 1.39 (t, J=7.2 Hz, 3H), 2.66-2.72 (m, 2H), 4.36 (q, J=7.2 Hz, 2H), 7.26 (d, J=7.2 Hz, 2H), 7.95 (d, J=7.2 Hz, 2H)

$^{13}$C-NMR (99 MHz, CDCl$_3$) δ: 0.3, 2.0, 14.3, 20.1, 29.6, 60.7, 127.8, 127.9, 129.6, 150.7, 166.7

[Example 17] Hydrosilylation of 2-Vinylnaphthalene with 1,1,3,3,3-Pentamethyldisiloxane Reaction was carried out according to the same procedure as in Example 11 aside from using 154 mg (1.0 mmol) of 2-vinylnaphthalene instead of styrene. As a result, it was confirmed that the signal assigned to the ethylene site of 2-vinylnaphthalene as the reactant disappeared completely. Instead, a multiplet at 0.89 ppm indicative of the signal assigned to proton on silicon-adjoining carbon in the desired product was observed, from which a yield was determined. The results are shown in Table 3.

Thereafter, the reaction solution was purified by silica gel column chromatography (developing solvent, hexane), obtaining 1,1,3,3,3-pentamethyl-3-(2-(2-naphthalenyl)ethyl)-disiloxane (175 mg, isolation yield 58%).

$^1$H-NMR (396 MHz, CDCl$_3$) δ: 0.10 (s, 9H), 0.10 (s, 6H), 0.95-1.02 (m, 2H), 2.78-2.84 (m, 2H), 7.33-7.47 (m, 3H), 7.62 (s, 1H), 7.74-7.82 (m, 3H)

$^{13}$C-NMR (99 MHz, CDCl$_3$) δ: 0.5, 2.2, 20.4, 29.8, 125.1, 125.6, 126.0, 127.2, 127.5, 127.7, 127.9, 132.1, 133.9, 142.9

TABLE 3

| | Substrate | Conversion (%) | Isolation yield (%) |
|---|---|---|---|
| Example 11 | styrene | >99 | |
| Example 12 | 4-methoxystyrene | 89 | |
| Example 13 | 4-t-butylstyrene | >99 | 99 |
| Example 14 | 4-chlorostyrene | >99 | 86 |
| Example 15 | 4-fluorostyrene | >99 | 89 |
| Example 16 | ethyl 4-vinylbenzoate | >99 | 96 |
| Example 17 | 2-vinylnaphthalene | 98 | 58 |

(5) Hydrosilylation 2 of Various Alkenes with 1,1,3,3,3-Pentamethyldisiloxane Using tBuNC Ligand

[Chemical Formula 12]

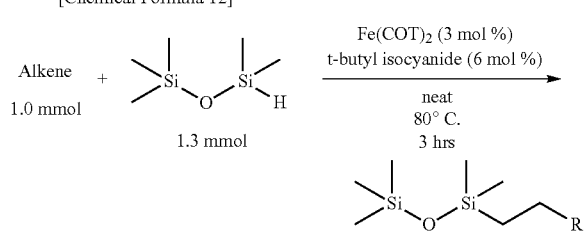

[Example 18] Hydrosilylation of 1-Octene with 1,1,3,3,3-Pentamethyldisiloxane

Reaction was carried out according to the same procedure as in Example 3 aside from using 157 μL (1.0 mmol) of 1-octene instead of styrene. As a result, it was confirmed that the signal assigned to the ethylene site of 1-octene as the reactant disappeared completely. Instead, a multiplet at 0.51 ppm indicative of the signal assigned to proton on silicon-adjoining carbon in the desired product was observed, from which a yield was determined. The results are shown in Table 4.

[Example 19] Hydrosilylation of 2-Octene with 1,1,3,3,3-Pentamethyldisiloxane

Reaction was carried out according to the same procedure as in Example 3 aside from using 157 μL (1.0 mmol) of 2-octene instead of styrene. As a result, it was confirmed that the signal assigned to the ethylene site of 2-octene as the reactant diminished. Instead, a multiplet at 0.51 ppm indicative of the signal assigned to proton on silicon-adjoining carbon in the desired product was observed, from which a yield was determined. The results are shown in Table 4.

$^1$H-NMR (396 MHz, CDCl$_3$) δ: 0.03 (s, 6H), 0.06 (s, 9H), 0.50 (t, J=7.7 Hz, 2H), 0.88 (t, J=6.8 Hz, 3H), 1.19-1.34 (m, 12H)

[Example 20] Hydrosilylation of 1,1,1,3,3-Pentamethyl-3-Vinyldisiloxane with 1,1,3,3,3-Pentamethyldisiloxane Reaction was carried out according to the same procedure as in Example 3 aside from using 222 μL (1.0 mmol) of 1,1,1,3,3-pentamethyl-3-vinyldisiloxane instead of styrene. As a result, it was confirmed that the signal assigned to the ethylene site of 1,1,1,3,3-pentamethyl-3-vinyldisiloxane as the reactant disappeared completely. Instead, a singlet at 0.40 ppm indicative of the signal assigned to proton on silicon-adjoining carbon in the desired product was observed, from which a yield was determined. The results are shown in Table 4.

$^1$H-NMR (396 MHz, CDCl$_3$) δ: 0.40 (s, 4H), 0.06 (s, 18H), 0.04 (s, 12H)

[Example 21] Hydrosilylation of Allylbenzene with 1,1,3,3,3-Pentamethyldisiloxane Reaction was carried out according to the same procedure as in Example 3 aside from using 133 μL (1.0 mmol) of allylbenzene instead of styrene. As a result, it was confirmed that the signal assigned to the ethylene site of allylbenzene as the reactant diminished. Instead, a multiplet at 0.56 ppm indicative of the signal assigned to proton on silicon-adjoining carbon in the desired product was observed, from which a yield was determined. The results are shown in Table 4.

$^1$H-NMR (396 MHz, CDCl$_3$) δ: 0.04 (s, 6H), 0.05 (s, 9H), 0.53-0.59 (m, 2H), 1.58-1.69 (m, 2H), 2.62 (t, J=6.8 Hz, 2H), 7.13-7.21 (m, 3H), 7.21-7.27 (m, 2H)

[Example 22] Hydrosilylation of α-Methylstyrene with 1,1,3,3,3-Pentamethyldisiloxane Reaction was carried out according to the same procedure as in Example 3 aside from using 130 μL (1.0 mmol) of α-methylstyrene instead of styrene. As a result, it was confirmed that the signal assigned to the ethylene site of α-methylstyrene as the reactant diminished. Instead, a multiplet at 0.95 ppm indicative of the signal assigned to proton on silicon-adjoining carbon in the desired product was observed, from which a yield was determined. The results are shown in Table 4.

$^1$H-NMR (396 MHz, CDCl$_3$) δ: −0.05 (s, 3H), −0.04 (s, 3H), 0.07 (s, 9H), 1.02-0.91 (m, 2H), 1.29 (d, J=6.8 Hz, 3H), 2.88-2.97 (m, 1H), 7.14-7.19 (m, 1H), 7.21-7.23 (m, 2H), 7.26-7.30 (m, 2H)

TABLE 4

| | Substrate | Conversion (%) | Yield (%) |
|---|---|---|---|
| Example 18 | 1-octene | >99 | 18 |
| Example 19 | 2-octene | 49 | 6 |
| Example 20 | 1,1,1,3,3-pentamethyl-3-vinyldisiloxane | >99 | 3 |
| Example 21 | allylbenzene | 85 | 21 |
| Example 22 | α-methylstyrene | 95 | 6 |

(6) Hydrosilylation of Cyclopentene with 1,1,3,3,3-Pentamethyldisiloxane Using tBuNC Ligand

[Chemical Formula 13]

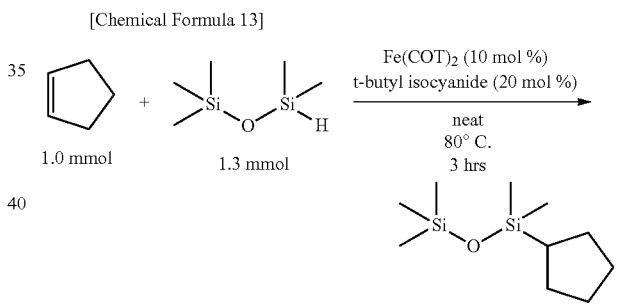

Example 23

In a nitrogen-blanketed glove box, 26 mg (0.10 mmol) of Fe(COT)$_2$ in Synthesis Example 2, 23 μL (0.20 mmol) of t-BuNC, 254 μL (1.3 mmol) of 1,1,3,3,3-pentamethyldisiloxane, and 88 μL (1.0 mmol) of cyclopentene were added to a screw-top vial with a stirrer. The vial was closed, after which the contents were stirred at 80° C. for 3 hours. After cooling, analysis was made by $^1$H-NMR spectroscopy to determine the structure and yield of the product. As a result, it was confirmed that the signal assigned to the ethylene site of cyclopentene as the reactant diminished. Instead, a multiplet near 0.86 ppm indicative of the signal assigned to proton on silicon-adjoining carbon in the desired product was observed, from which a yield was computed. The results are shown in Table 5.

$^1$H-NMR (396 MHz, CDCl$_3$) δ: 0.02 (s, 6H), 0.06 (s, 9H), 1.20-1.36 (m, 2H), 0.83-0.92 (m, 1H), 1.50-1.57 (m, 4H), 1.66-1.85 (m, 2H)

TABLE 5

| | Conversion (%) | Yield (%) |
|---|---|---|
| Example 23 | 79 | 18 |

(7) Hydrosilylation 2 of Styrene with 1,1,3,3,3-Pentamethyldisiloxane Using tBuNC Ligand

[Chemical Formula 14]

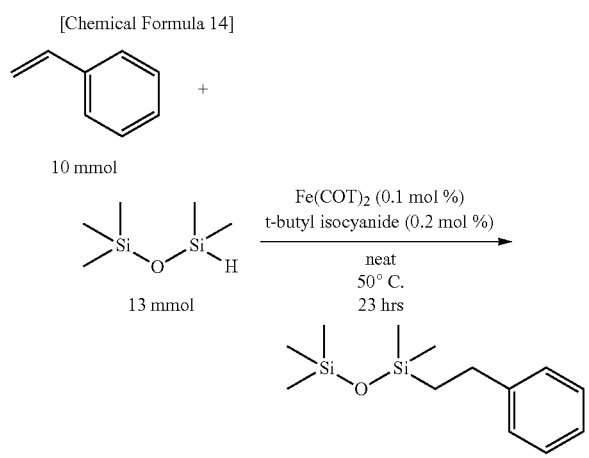

[Example 24] Reduction of Catalyst Amount from Example 11

In a nitrogen-blanketed glove box, 3 mg (0.01 mmol) of Fe(COT)$_2$ in Synthesis Example 2, 2 μL (0.06 mmol) of tBuNC, 1.94 g (13.0 mmol) of 1,1,3,3,3-pentamethyldisiloxane, and 1.04 g (10.0 mmol) of styrene were added to a screw-top vial with a stirrer. The vial was closed, after which the contents were stirred at 50° C. for 24 hours. After cooling, analysis was made by $^1$H-NMR spectroscopy to determine the structure and yield of the product. As a result, it was confirmed that the signal assigned to the reactant disappeared completely. Instead, a multiplet near 0.86 ppm indicative of the signal assigned to the desired product was observed, from which a yield was computed. The results are shown in Table 6.

Thereafter, the reaction solution was passed through an alumina column to remove the catalyst and purified by distillation at a vacuum of 3 Pa and 40° C., obtaining a clear solution (2.36 g (9.35 mmol), isolation yield 94%).

$^1$H-NMR (396 MHz, CDCl$_3$) δ: 0.08 (s, 6H), 0.10 (s, 9H), 0.87-0.93 (m, 2H), 2.62-2.69 (m, 2H), 7.14-7.23 (m, 3H), 7.28 (t, J=7.2 Hz, 2H)

$^{13}$C-NMR (99 MHz, CDCl$_3$) δ: 0.3, 2.0, 20.4, 29.4, 125.5, 127.8, 128.3, 145.2

TABLE 6

| | Yield | Isolation yield |
|---|---|---|
| Example 24 | >99 | 94% |

(8) Hydrosilylation of Styrene with Various Hydrosilanes Using tBuNC Ligand

[Chemical Formula 15]

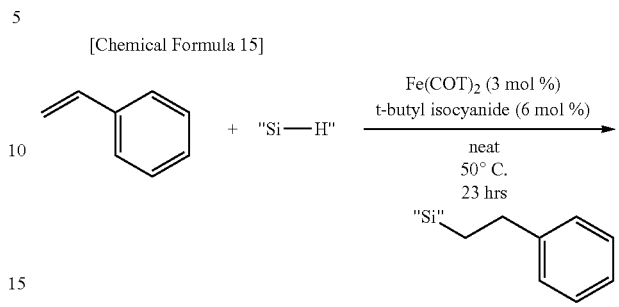

[Example 25] Hydrosilylation of Styrene with Dimethylphenylsilane

Reaction was carried out according to the same procedure as in Example 11 aside from using 202 μL (1.3 mmol) of dimethylphenylsilane instead of 1,1,3,3,3-pentamethyldisiloxane. As a result, it was confirmed that the signal assigned to the ethylene site of styrene as the reactant disappeared completely. Instead, a multiplet at 1.13 ppm indicative of the signal assigned to proton on silicon-adjoining carbon in the desired product, dimethyl(phenethyl)phenylsilane was observed, from which a yield was computed. The results are shown in Table 7.

$^1$H-NMR (396 MHz, CDCl$_3$) δ: 0.29 (s, 6H), 1.10-1.16 (m, 2H), 2.61-2.67 (m, 2H), 7.13-7.39 (m, 8H9, 7.51-7.56 (m, 2H)

[Example 26] Hydrosilylation of Styrene with Dual End Dimethylhydrosilyl-Blocked Polydimethylsiloxane In a nitrogen-blanketed glove box, 16 mg (0.06 mmol) of Fe(COT)$_2$ in Synthesis Example 2, 14 μL (0.12 mmol) of tBuNC, 2.77 g (1.3 mmol) of dual end dimethylhydrosilyl-blocked polydimethylsiloxane (n=27), and 230 μL (2.0 mmol) of styrene were added to a screw-top vial with a stirrer. The vial was closed, after which the contents were stirred at 50° C. for 23 hours. After cooling, analysis was made by $^1$H-NMR spectroscopy to determine the structure and yield of the product. As a result, it was confirmed that the signal assigned to the ethylene site of styrene as the reactant disappeared completely. Instead, a multiplet at 0.91 ppm indicative of the signal assigned to proton on silicon-adjoining carbon in the desired product was observed, from which a yield was computed. The results are shown in Table 7.

$^1$H-NMR (396 MHz, CDCl$_3$) δ: 0.07 (br), 0.88-0.95 (m, 4H), 2.62-2.69 (m, 4H), 7.13-7.33 (m, 10H)

TABLE 7

| | Compound containing Si—H group | Conversion (%) | Yield (%) |
|---|---|---|---|
| Example 25 | dimethylphenylsilane | >99 | 89 |
| Example 26 | dual end dimethylhydrosilyl-blocked polydimethylsiloxane | >99 | 94 |

(9) Hydrosilylation of Various Alkenes with 1,1,3,3,3-Pentamethyldisiloxane Using AdNC Ligand

[Chemical Formula 16]

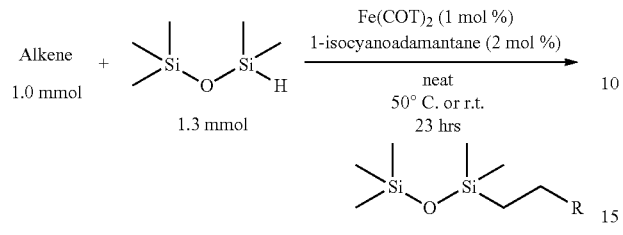

Example 27

In a nitrogen-blanketed glove box, 2 mg (0.01 mmol) of Fe(COT)$_2$ in Synthesis Example 2, 3 mg (0.02 mmol) of AdNC, 254 μL (1.3 mmol) of 1,1,3,3,3-pentamethyldisiloxane, and 115 μL (1.0 mmol) of styrene were added to a screw-top vial with a stirrer. The vial was closed, after which the contents were stirred at room temperature (RT) for 23 hours. After cooling, analysis was made by $^1$H-NMR spectroscopy to determine the structure and yield of the product. As a result, it was confirmed that the signal assigned to the reactant disappeared completely. Instead, a multiplet near 0.89 ppm indicative of the signal assigned to the desired product was observed, from which a yield was computed. The results are shown in Table 8.

Examples 28 to 33

Reaction was carried out according to the same procedure as in Example 27 aside from using 1.0 mmol of the alkenes listed in Table 8 instead of styrene and in Examples 28 and 33, changing to the temperature shown in Table 8. The results are shown in Table 8.

TABLE 8

| | Substrate | Reaction temperature | Conversion (%) | Yield (%) |
|---|---|---|---|---|
| Example 27 | styrene | RT | >99 | >99 |
| Example 28 | 4-methoxystyrene | 50° C. | >99 | 96 |
| Example 29 | 4-t-butylstyrene | RT | >99 | >99 |
| Example 30 | 4-chlorostyrene | RT | >99 | >99 |
| Example 31 | 4-fluorostyrene | RT | 62 | 62 |
| Example 32 | ethyl 4-vinylbenzoate | RT | 38 | 38 |
| Example 33 | 2-vinylnaphthalene | 50° C. | >99 | >99 |

(10) Hydrosilylation of Styrene with Various Hydrosilanes Using AdNC Ligand

[Chemical Formula 17]

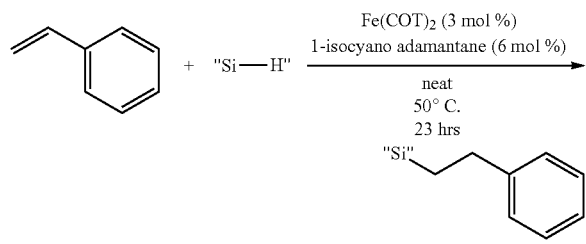

[Example 34] Hydrosilylation of Styrene with Dimethylphenylsilane

Reaction was carried out according to the same procedure as in Example 25 aside from using 10 mg (0.06 mmol) of AdNC instead of tBuNC. As a result, it was confirmed that the signal assigned to the reactant disappeared completely. Instead, a multiplet at 1.13 ppm indicative of the signal assigned to proton on the desired product was observed, from which a yield was computed. The results are shown in Table 9.

[Example 35] Hydrosilylation of Styrene with Dual End Dimethylhydrosilyl-Blocked Polydimethylsiloxane Reaction was carried out according to the same procedure as in Example 26 aside from using 20 mg (0.12 mmol) of AdNC instead of tBuNC. As a result, it was confirmed that the signal assigned to the reactant disappeared completely. Instead, a multiplet at 0.91 ppm indicative of the signal assigned to the desired product was observed, from which a yield was computed. The results are shown in Table 9.

TABLE 9

| | Compound containing Si—H group | Conversion (%) | Yield (%) |
|---|---|---|---|
| Example 34 | dimethylphenylsilane | >99 | 90 |
| Example 35 | dual end dimethylhydrosilyl-blocked polydimethylsiloxane | >99 | >99 |

(11) Hydrosilylation of Styrene with 1,1,3,3,3-Pentamethyldisiloxane Using Bisiminopyridine Ligand

[Chemical Formula 18]

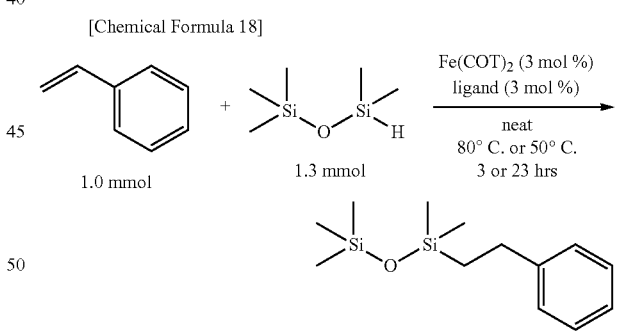

Examples 36 to 38

A screw-top vial was charged with 8 mg (0.03 mmol) of Fe(COT)$_2$ in Synthesis Example 2, 0.03 mmol of the ligand listed in Table 10, 254 μL (1.3 mmol) of 1,1,3,3,3-pentamethyldisiloxane, and 115 μL (1.0 mmol) of styrene. The vial was closed, after which reaction was conducted under the conditions shown in Table 10. After cooling, analysis was made by $^1$H-NMR spectroscopy to determine the structure and yield of the product. As a result, it was confirmed that the signal assigned to the reactant diminished. Instead, a multiplet near 0.89 ppm indicative of the signal assigned to the desired product was observed. A conversion and yield were determined from the ¹H-NMR data. The results are shown in Table 10.

TABLE 10

|  | Ligand | Temp. (° C.) | Time (hrs) | Conversion (%) | Yield (%) |
|---|---|---|---|---|---|
| Example 36 | MePDI (11 mg) (0.03 mmol) | 80 | 3 | 75 | 75 |
| Example 37 | MePDI (11 mg) (0.03 mmol) | 50 | 23 | 85 | 85 |
| Example 38 | EtPDI (13 mg) (0.03 mmol) | 80 | 3 | 46 | 46 |

MePDI: 2,6-bis[1-(2,6-dimethylphenylimino)ethyl]pyridine
EtPDI: 2,6-bis[1-(2,6-diethylphenylimino)ethyl]pyridine

(12) Hydrosilylation of 1-Octene with 1,1,3,3,3-Pentamethyldisiloxane Using Bisiminopyridine Ligand

[Chemical Formula 19]

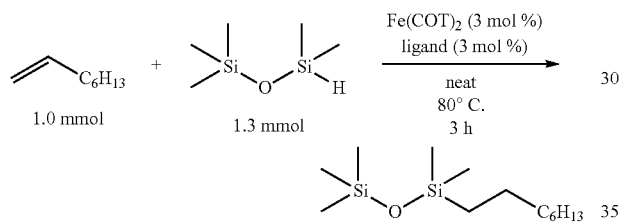

Example 39

Reaction was carried out according to the same procedure as in Example 36 aside from using 157 μL (1.0 mmol) of 1-octene instead of styrene. As a result, it was confirmed that the signal assigned to the reactant diminished. Instead, a multiplet at 0.51 ppm indicative of the signal assigned to the desired product was observed. A conversion and yield were determined from the ¹H-NMR data. The results are shown in Table 11.

Example 40

Reaction was carried out according to the same procedure as in Example 38 aside from using 157 μL (1.0 mmol) of 1-octene instead of styrene. As a result, it was confirmed that the signal assigned to the reactant diminished. Instead, a multiplet at 0.51 ppm indicative of the signal assigned to the desired product was observed. A conversion and yield were determined from the ¹H-NMR data. The results are shown in Table 11.

TABLE 11

|  | Ligand | Conversion (%) | Yield (%) |
|---|---|---|---|
| Example 39 | MePDI (11 mg) (0.03 mmol) | 58 | 58 |
| Example 40 | EtPDI (13 mg) (0.03 mmol) | 63 | 37 |

(13) Hydrosilylation of Styrene with 1,1,3,3,3-Pentamethyldisiloxane Using Various Iron Precursors and tBuNC Ligand

[Chemical Formula 20]

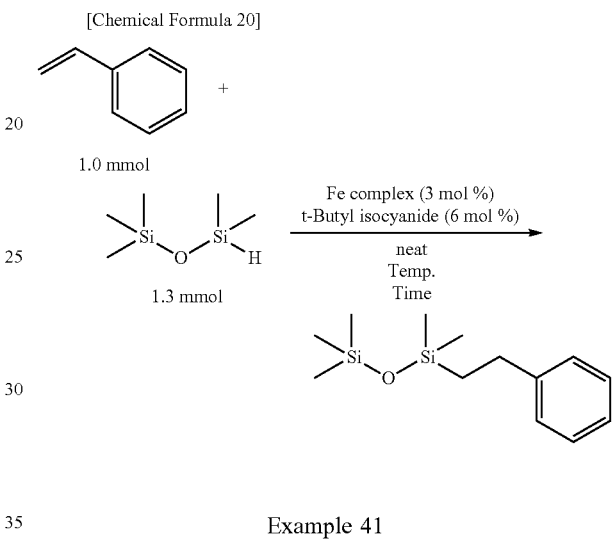

Example 41

A screw-top vial was charged with 7 mg (0.03 mmol) of (MPDE)₂Fe in Synthesis Example 3, 7 μL (0.06 mmol) of tBuNC, 254 μL (1.3 mmol) of 1,1,3,3,3-pentamethyldisiloxane, and 115 μL (1.0 mmol) of styrene. The vial was closed, after which the contents were stirred at 80° C. for 3 hours. After cooling, analysis was made by ¹H-NMR spectroscopy to determine the structure and yield of the product. As a result, it was confirmed that the signal assigned to the reactant disappeared completely. Instead, a multiplet near 0.89 ppm indicative of the signal assigned to proton in the desired product was observed, from which a yield was determined. The results are shown in Table 12.

Example 42

Reaction was carried out according to the same procedure as in Example 41 aside from using 7 mg (0.03 mmol) of (DMPDE)₂Fe in Synthesis Example 4 instead of (MPDE)₂Fe. As a result, it was confirmed that the signal assigned to the ethylene site of styrene as the reactant disappeared completely. Instead, a multiplet near 0.89 ppm indicative of the signal assigned to proton on silicon-adjoining carbon in the desired product, 1,1,1,3,3-pentamethyl-3-phenethyldisiloxane was observed, from which a yield was determined. The results are shown in Table 12.

Example 43

A screw-top vial was charged with like amounts of like reactants as in Example 41. The vial was closed, after which the contents were stirred at 50° C. for 23 hours. After cooling, analysis was made by $^1$H-NMR spectroscopy to determine the structure and yield of the product. As a result, it was confirmed that the signal assigned to the ethylene site of styrene as the reactant disappeared completely. Instead, a multiplet near 0.89 ppm indicative of the signal assigned to the desired product was observed, from which a yield was determined. The results are shown in Table 12.

TABLE 12

| | Precursor | Temp. (° C.) | Time (hrs) | Conversion (%) | Yield (%) |
|---|---|---|---|---|---|
| Example 41 | (MPDE)$_2$Fe in Synthesis Example 3 | 80 | 3 | >99 | 51 |
| Example 42 | (DMPDE)$_2$Fe in Synthesis Example 4 | 80 | 3 | >99 | 71 |
| Example 43 | (MPDE)$_2$Fe in Synthesis Example 3 | 50 | 23 | >99 | >99 |

(14) Hydrosilylation of 1-Octene with 1,1,3,3,3-Pentamethyldisiloxane Using Iron Precursor and NHC Ligand

[Chemical Formula 21]

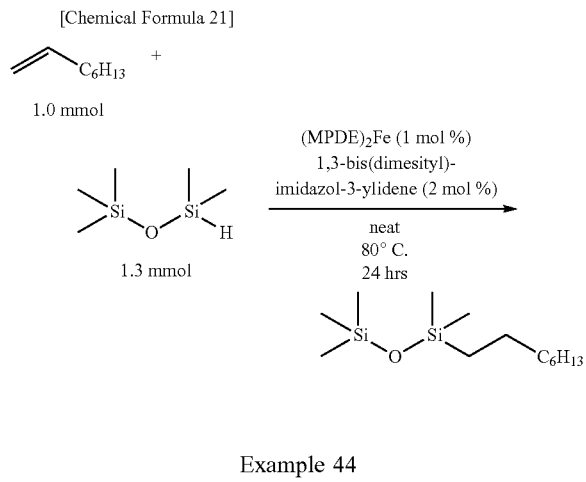

Example 44

A screw-top vial was charged with 2 mg (0.01 mmol) of (MPDE)$_2$Fe in Synthesis Example 3, 6 mg (0.02 mmol) of 1,3-dimesitylimidazol-2-ylidene, 254 μL (1.3 mmol) of 1,1,3,3,3-pentamethyldisiloxane, and 157 μL (1.0 mmol) of 1-octene. The vial was closed, after which the contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet near 0.89 ppm indicative of the signal assigned to the desired product was observed, from which a yield was determined. The results are shown in Table 13.

TABLE 13

| | Precursor | Conversion (%) | Yield (%) |
|---|---|---|---|
| Example 44 | (MPDE)$_2$Fe in Synthesis Example 3 | >99 | 48 |

(15) Hydrosilylation of Styrene with 1,1,3,3,3-Pentamethyldisiloxane Using Various Iron Complexes

[Chemical Formula 22]

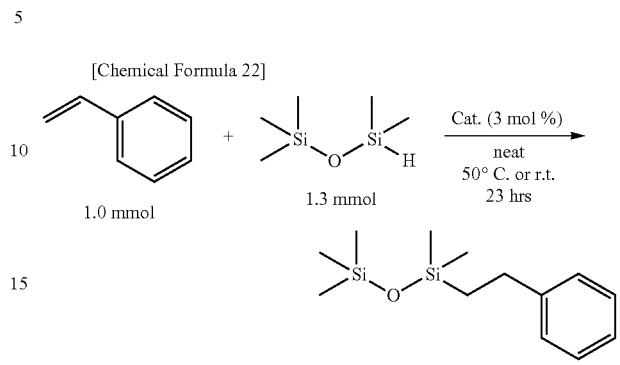

Examples 45 to 48

In a nitrogen-blanketed glove box, 0.03 mmol of the iron catalyst listed in Table 14, 254 μL (1.3 mmol) of 1,1,3,3,3-pentamethyldisiloxane, and 115 μL (1.0 mmol) of styrene were added to a screw-top vial with a stirrer. The vial was closed, after which reaction was run under the conditions shown in Table 14. After cooling, analysis was made by $^1$H-NMR spectroscopy to determine the structure and yield of the product. As a result, it was confirmed that the signal assigned to the reactant disappeared completely. Instead, a multiplet near 0.89 ppm indicative of the signal assigned to the desired product was observed. A yield was computed from the $^1$H-NMR data. The results are shown in Table 14.

TABLE 14

| | Catalyst (amount) (mmol) | Temp. (° C.) | Time (hrs) | Conversion (%) | Yield (%) |
|---|---|---|---|---|---|
| Example 45 | Iron complex A (10 mg) (0.03) | 50 | 23 | >99 | 89 |
| Example 46 | Iron complex B (13 mg) (0.03) | RT | 23 | 17 | 17 |
| Example 47 | Iron complex C (12 mg) (0.03) | 50 | 23 | >99 | 97 |
| Example 48 | Iron complex D (19 mg) (0.03) | RT | 23 | 33 | 33 |

(16) Hydrosilylation of Alkene with 1,1,3,3,3-Pentamethyldisiloxane Using Various Iron Precursors and Various Ligands Example 49

Reaction was conducted as in Example 11 by using 3 mg (0.01 mmol) of iron biscyclooctatetraene in Synthesis Example 2, 3 μL (0.02 mmol) of tBuNC, 254 μL (1.3 mmol) of 1,1,3,3,3-pentamethyldisiloxane, and 115 μL (1.0 mmol) of styrene and stirring the contents at 50° C. for 3 hours. The yield of the desired product was 99% when determined as in Example 3.

Example 50

Reaction was conducted as in Example 11 by using 3 mg (0.01 mmol) of iron biscyclooctatetraene in Synthesis Example 2, 3 mg (0.02 mmol) of AdNC, 254 µL (1.3 mmol) of 1,1,3,3,3-pentamethyldisiloxane, and 115 µL (1.0 mmol) of styrene and stirring the contents at 50° C. for 0.5 hour. The yield of the desired product was 99% when determined as in Example 3.

Example 51

Reaction was conducted as in Example 11 by using 2 mg (0.01 mmol) of iron bis(3-methylpentadienyl) in Synthesis Example 3, 3 µL (0.02 mmol) of tBuNC, 254 µL (1.3 mmol) of 1,1,3,3,3-pentamethyldisiloxane, and 115 µL (1.0 mmol) of styrene and stirring the contents at 50° C. for 6 hours. The yield of the desired product was 99% when determined as in Example 3.

Example 52

Reaction was conducted as in Example 11 by using 2 mg (0.01 mmol) of iron bis(3-methylpentadienyl) in Synthesis Example 3, 3 mg (0.02 mmol) of AdNC, 254 µL (1.3 mmol) of 1,1,3,3,3-pentamethyldisiloxane, and 115 µL (1.0 mmol) of styrene and stirring the contents at 50° C. for 6 hours. The yield of the desired product was 99% when determined as in Example 3.

Example 53

Reaction was conducted as in Example 11 by using 2 mg (0.01 mmol) of iron bis(3-methylpentadienyl) in Synthesis Example 3, 3 mg (0.02 mmol) of AdNC, 2.54 mL (13.0 mmol) of 1,1,3,3,3-pentamethyldisiloxane, and 1.15 mL (10.0 mmol) of styrene and stirring the contents at 50° C. for 23 hours. The yield of the desired product was 99% when determined as in Example 3.

Example 54

Reaction was conducted as in Example 3 by using 2 mg (0.01 mmol) of iron bis(3-methylpentadienyl) in Synthesis Example 3, 4 mg (0.01 mmol) of MePDI, 254 µL (1.3 mmol) of 1,1,3,3,3-pentamethyldisiloxane, and 115 µL (1.0 mmol) of styrene and stirring the contents at 80° C. for 3 hours. The yield of the desired product was 99% when determined as in Example 3.

Example 55

Reaction was conducted as in Example 3 by using 2 mg (0.01 mmol) of iron bis(3-methylpentadienyl) in Synthesis Example 3, 4 mg (0.01 mmol) of EtPDI, 254 µL (1.3 mmol) of 1,1,3,3,3-pentamethyldisiloxane, and 115 µL (1.0 mmol) of styrene and stirring the contents at 80° C. for 3 hours. The yield of the desired product was 99% when determined as in Example 3.

Example 56

Reaction was conducted as in Example 3 by using 2 mg (0.01 mmol) of iron bis(3-methylpentadienyl) in Synthesis Example 3, 5 mg (0.01 mmol) of 2,6-bis[1-(2,6-diisopropylphenylimino)ethyl]pyridine (iPrPDI), 254 µL (1.3 mmol) of 1,1,3,3,3-pentamethyldisiloxane, and 115 µL (1.0 mmol) of styrene and stirring the contents at 80° C. for 3 hours. The conversion was 40% and the yield of the desired product was 34% when determined as in Example 3.

Example 57

Reaction was conducted as in Example 3 by using 2 mg (0.01 mmol) of iron bis(3-methylpentadienyl) in Synthesis Example 3, 2 mg (0.01 mmol) of 2,2':6',2''-terpyridine, 254 µL (1.3 mmol) of 1,1,3,3,3-pentamethyldisiloxane, and 115 µL (1.0 mmol) of styrene and stirring the contents at 80° C. for 3 hours. The conversion was 24% and the yield of the desired product was 18% when determined as in Example 3.

Example 58

Reaction was conducted as in Example 1 by using 2 mg (0.01 mmol) of iron bis(3-methylpentadienyl) in Synthesis Example 3, 4 mg (0.01 mmol) of MePDI, 254 µL (1.3 mmol) of 1,1,3,3,3-pentamethyldisiloxane, and 157 µL (1.0 mmol) of 1-octene and stirring the contents at 80° C. for 3 hours. The conversion was at least 99% and the yield of the desired product was 67% when determined as in Example 1.

Example 59

Reaction was conducted as in Example 1 by using 2 mg (0.01 mmol) of iron bis(3-methylpentadienyl) in Synthesis Example 3, 4 mg (0.01 mmol) of EtPDI, 254 µL (1.3 mmol) of 1,1,3,3,3-pentamethyldisiloxane, and 157 µL (1.0 mmol) of 1-octene and stirring the contents at 80° C. for 3 hours. The conversion was at least 99% and the yield of the desired product was 85% when determined as in Example 1.

Example 60

Reaction was conducted as in Example 1 by using 2 mg (0.01 mmol) of iron bis(3-methylpentadienyl) in Synthesis Example 3, 5 mg (0.01 mmol) of iPrPDI, 254 µL (1.3 mmol) of 1,1,3,3,3-pentamethyldisiloxane, and 157 µL (1.0 mmol) of 1-octene and stirring the contents at 80° C. for 3 hours. The conversion was at least 99% and the yield of the desired product was 76% when determined as in Example 1.

Example 61

Reaction was conducted as in Example 1 by using 2 mg (0.01 mmol) of iron bis(3-methylpentadienyl) in Synthesis Example 3, 2 mg (0.01 mmol) of 2,2':6',2''-terpyridine, 254 µL (1.3 mmol) of 1,1,3,3,3-pentamethyldisiloxane, and 157 µL (1.0 mmol) of 1-octene and stirring the contents at 80° C. for 3 hours. The conversion was 75% and the yield of the desired product was 34% when determined as in Example 1.

Example 62

Reaction was conducted as in Example 28 by using 7 mg (0.03 mmol) of iron bis(3-methylpentadienyl) in Synthesis Example 3, 7 µL (0.06 mmol) of tBuNC, 254 µL (1.3 mmol) of 1,1,3,3,3-pentamethyldisiloxane, and 127 µL (1.0 mmol) of 4-chlorostyrene and stirring the contents at 50° C. for 23 hours. The yield of the desired product was 99% when determined as in Example 28.

Example 63

Reaction was conducted as in Example 28 by using 7 mg (0.03 mmol) of iron bis(3-methylpentadienyl) in Synthesis Example 3, 10 mg (0.06 mmol) of AdNC, 254 μL (1.3 mmol) of 1,1,3,3,3-pentamethyldisiloxane, and 127 μL (1.0 mmol) of 4-chlorostyrene and stirring the contents at 50° C. for 23 hours. The yield of the desired product was 99% when determined as in Example 28.

Example 64

Reaction was conducted as in Example 28 by using 7 mg (0.03 mmol) of iron bis(3-methylpentadienyl) in Synthesis Example 3, 7 μL (0.06 mmol) of tBuNC, 254 μL (1.3 mmol) of 1,1,3,3,3-pentamethyldisiloxane, and 134 μL (1.0 mmol) of 4-methoxystyrene and stirring the contents at 50° C. for 23 hours. The yield of the desired product was 89% when determined as in Example 28.

Example 65

Reaction was conducted as in Example 28 by using 7 mg (0.03 mmol) of iron bis(3-methylpentadienyl) in Synthesis Example 3, 10 mg (0.06 mmol) of AdNC, 254 μL (1.3 mmol) of 1,1,3,3,3-pentamethyldisiloxane, and 134 μL (1.0 mmol) of 4-methoxystyrene and stirring the contents at 50° C. for 23 hours. The yield of the desired product was 99% when determined as in Example 28.

The invention claimed is:

1. A hydrosilylation iron catalyst which is prepared from a two-electron ligand (L) and a mono-, bi- or tri-nuclear complex of iron having the formula (1):

$$Fe(X)_a \quad (1)$$

wherein
each X is independently a $C_2$-$C_{30}$ ligand which may contain an unsaturated group, exclusive of carbonyl (CO) and cyclopentadienyl groups, at least one X contains an unsaturated group,
a is an integer of 2 to 4 per Fe atom, and
Fe has bonds with carbon atoms in X, the total number of Fe-carbon bonds being 2 to 10, and Fe bonds solely with carbon atoms in X.

2. A hydrosilylation iron catalyst consisting of a mixture of a two-electron ligand (L) and a mono-, bi- or tri-nuclear complex of iron having the formula (1):

$$Fe(X)_a \quad (1)$$

wherein
each X is independently a $C_2$-$C_{30}$ ligand which may contain an unsaturated group, exclusive of carbonyl (CO) and cyclopentadienyl groups, at least one X contains an unsaturated group,
a is an integer of 2 to 4 per Fe atom, and
Fe has bonds with carbon atoms in X, the total number of Fe-carbon bonds being 2 to 10.

3. The hydrosilylation iron catalyst of claim 1 or 2 wherein each X is a $C_2$-$C_{30}$ ligand containing an unsaturated group.

4. The hydrosilylation iron catalyst of claim 1 wherein X is an aryl group, and the total number of Fe-carbon bonds is 2.

5. The hydrosilylation iron catalyst of claim 1 which is a mononuclear complex wherein the total number of Fe-carbon bonds is 6 to 10.

6. The hydrosilylation iron catalyst of claim 5 wherein the total number of Fe-carbon bonds is 10.

7. The hydrosilylation iron catalyst of claim 5 or 6 wherein X is at least one ligand selected from a cyclic olefin, acyclic olefin, cyclic olefinyl and acyclic olefinyl group having 1 to 5 unsaturated groups in the molecule.

8. The hydrosilylation iron catalyst of claim 1 wherein L is at least one two-electron ligand selected from the group consisting of carbonyl, molecular hydrogen, amine, imine, nitrogen-containing heterocycle, phosphine, arsine, alcohol, thiol, ether, sulfide, nitrile, isocyanide, aldehyde, ketone, and carbene.

9. The hydrosilylation iron catalyst of claim 8 wherein L is at least one two-electron ligand selected from the group consisting of molecular hydrogen, amine, imine, nitrogen-containing heterocycle, phosphine, arsine, alcohol, thiol, ether, sulfide, nitrile, isocyanide, aldehyde, ketone, and carbene.

10. The hydrosilylation iron catalyst of claim 9 wherein L is at least one two-electron ligand selected from the group consisting of nitrogen-containing heterocycle, isocyanide, and carbene.

11. The hydrosilylation iron catalyst of claim 10 wherein L is at least one two-electron ligand selected from
an isocyanide compound having the formula (2):

$$Y-NC \quad (2)$$

wherein Y is an optionally substituted $C_1$-$C_{30}$ monovalent organic group which may be separated by at least one atom selected from oxygen, nitrogen, sulfur and phosphorus, and
a carbene compound having one or two adjoining nitrogen atoms, represented by the formula (3):

(3)

wherein Z is a carbon, nitrogen or oxygen atom, b is 3 when Z is a carbon atom, b is 2 when Z is a nitrogen atom, b is 1 when Z is an oxygen atom, $R^1$ and $R^2$ are each independently a $C_1$-$C_{30}$ alkyl, aryl or aralkyl group which may be substituted with a halogen atom or alkoxy group, any one of $R^1$ and any one of $R^2$ may bond together to form a divalent organic group so that the compound has a cyclic structure, and the compound having a cyclic structure may contain a nitrogen atom and/or unsaturated bond.

12. The hydrosilylation iron catalyst of claim 11 wherein the carbene compound of formula (3) has the formula (4):

(4)

wherein A is a $C_2$-$C_5$ divalent organic group which may contain a nitrogen atom and/or unsaturated bond, $R^1$ and $R^2$ are each independently a $C_1$-$C_{30}$ alkyl, aryl or aralkyl group which may be substituted with a halogen atom or alkoxy group.

13. The hydrosilylation iron catalyst of claim 10 wherein L is a bisiminopyridine compound or terpyridine compound.

14. The hydrosilylation iron catalyst of claim 1 which is prepared in a system where hydrosilylation reaction of a compound having an aliphatic unsaturated bond with a hydrosilane compound having a Si—H group or organohydropolysiloxane compound is carried out.

15. A method for preparing an addition compound comprising the step of carrying out hydrosilylation reaction of a compound having an aliphatic unsaturated bond with a hydrosilane compound having a Si—H bond or organohydropolysiloxane compound in the presence of the hydrosilylation iron catalyst of claim 1.

16. The method for preparing an addition compound of claim 15 wherein the compound having an aliphatic unsaturated bond is an organopolysiloxane having an alkenyl group.

* * * * *